US009827247B2

United States Patent
Dave et al.

(10) Patent No.: US 9,827,247 B2
(45) Date of Patent: *Nov. 28, 2017

(54) HETEROCYCLYL COMPOUNDS

(71) Applicant: LUPIN LIMITED, Mumbai (IN)

(72) Inventors: Bhavesh Dave, Pune (IN); Rakesh Kumar Banerjee, Pune (IN); Samiron Phukan, Pune (IN); Abhijit Datta Khoje, Pune (IN); Rajkumar Hangarge, Pune (IN); Jitendra Sambhaji Jadhav, Pune (IN); Venkata P. Palle, Pune (IN); Rajender Kumar Kamboj, Pune (IN)

(73) Assignee: Lupin Limited, Mumbai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 15/400,627

(22) Filed: Jan. 6, 2017

(65) Prior Publication Data

US 2017/0112840 A1    Apr. 27, 2017

Related U.S. Application Data

(63) Continuation of application No. 14/385,106, filed as application No. PCT/IB2013/051915 on Mar. 11, 2013, now Pat. No. 9,573,944.

(30) Foreign Application Priority Data

Mar. 14, 2012    (IN) .............................. 288/KOL/2012

(51) Int. Cl.
*A61K 31/519*    (2006.01)
*C07D 471/04*    (2006.01)
*A61K 45/06*    (2006.01)

(52) U.S. Cl.
CPC ............ *A61K 31/519* (2013.01); *A61K 45/06* (2013.01)

(58) Field of Classification Search
None
See application file for complete search history.

(56) References Cited

U.S. PATENT DOCUMENTS

| 4,235,871 A | 11/1980 | Papahadjopoulos et al. |
| 4,501,728 A | 2/1985 | Geho et al. |
| 4,837,028 A | 6/1989 | Allen et al. |
| 5,019,369 A | 5/1991 | Presant et al. |
| 2006/0014768 A1 | 1/2006 | Kawasaki et al. |
| 2015/0133424 A1 | 5/2015 | Dave et al. |
| 2015/0299186 A1 | 10/2015 | Dave et al. |

FOREIGN PATENT DOCUMENTS

| WO | 03/053960 A1 | 7/2003 |
| WO | 2005/023251 A1 | 3/2005 |
| WO | 2005/051906 A1 | 6/2005 |
| WO | 2005/121142 A1 | 12/2005 |
| WO | 2010/121646 A1 | 10/2010 |

OTHER PUBLICATIONS

Thaisrivongs et al., "Structure-Based Design of Novel HIV Protease Inhibitors: Carboxamide-Containing 4-Hydroxycoumarins and 4-Hydroxy-2-pyrones as Potent Nonpeptidic Inhibitors", Journal of Medicinal Chemistry, 1995, vol. 38, pp. 3624-3637.
Hanahan et al., "The Hallmarks of Cancer", Cell, Jan. 7, 2000, vol. 100, pp. 57-70.
Hanahan et al., "Hallmarks of Cancer: The Next Generation", Cell, Mar. 4, 2011, vol. 144, pp. 646-674.
Sebolt-Leopold et al., "Targeting the Mitogen-activated Protein Kinase Cascade to Treat Cancer", Nature Reviews, Cancer, Dec. 2004, vol. 4, pp. 937-947.
Fukazawa et al., "Mitogen-activated Protein/Extracellular Signal-regulated Kinase Kinase (MEK) Inhibitors Restore Anoikis Sensitivity in Human Breast Cancer Cell Lines with a Constitutively Activated Extracellular-regulated Kinase (ERK) Pathway", Molecular Cancer Therapeutics, Mar. 2002, vol. 1, pp. 303-309.
McCubrey et al., "Targeting the Raf/MEK/ERK pathway with small-molecule inhibitors", Current Opinion in Investigational Drugs, 2008, vol. 9., No. 6, pp. 614-630.
Kyriakis et al., "Sounding the Alarm: Protein Kinase Cascades Activated by Stress and Inflammation", The Journal of Biological Chemistry, 1996, vol. 271, No. 40, pp. 24313-24316.
Hammaker et al., "Regulation of c-Jun N-Terminal Kinase by MEKK-2 and Mitogen-Activated Protein Kinase Kinase Kinases in Rheumatoid Arthritis", The Journal of Immunology, 2004, vol. 172, pp. 1612-1618.
Berge et al., "Pharmaceutical Salts", Review article in Journal of Pharmaceutical Sciences, Jan. 1977, vol. 66, No. 1, pp. 1-19.
Remington's Pharmaceutical Sciences, 18th Edition, Mack Publishing Company, Easton, PA, 1990, p. 1445.

(Continued)

*Primary Examiner* — Deepak R Rao
*Assistant Examiner* — Laura M Daniel
(74) *Attorney, Agent, or Firm* — Melissa M. Hayworth; Daniel R. Evans; E. Joseph Gess

(57) ABSTRACT

The present invention is related to heteroaryl compounds as MEK inhibitors. The invention includes heteroaryl compounds of formula I, their tautomers and pharmaceutically acceptable salts, combinations with suitable medicament and pharmaceutical compositions thereof. The present invention also includes process of preparation of the said compounds and intended use in therapy of them.

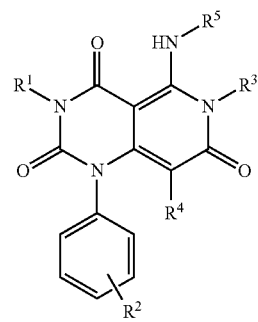

(I)

32 Claims, No Drawings

(56) References Cited

OTHER PUBLICATIONS

G. Banker, "Pharmaceutics and Pharmacy Practice", J.B. Lippincott Company, Philadelphia, PA, 1982, pp. 238-250.
L. A. Trissel, "Injectable Drugs", 4th Edition, ASHP Handbook, Sep. 1986, pp. 622-630.
Remington's Pharmaceutical Sciences, 17th Edition, Chapter 85 and 86, Mack Publishing Company, Easton, PA, 1985, pp. 1518-1552.
F. Szoka, Jr, "Comparative Properties and Methods of Preparation of Lipid Vesicles (Liposomes)", Ann. Rev. Biophys. Bioeng., 1980, vol. 9, pp. 467-508.
Physician's Desk Reference, 58th Edition, Thomson PDR, 2004.
Wasserman et al. "Clinical Comparison of the Nitrosoureas", Cancer, 1975, vol. 36, pp. 1258-1268.
Stahl et al., "Handbook of Pharmaceutical Salts Properties, Selection, and Use", WILEY-VCH, 2002.
International Search Report for corresponding Application No. PCT/IB2013/051915, dated Apr. 25, 2013.
M. Thiel, "Arthritis & Rheumatism", 2007, vol. 56, No. 10, pp. 3347-3357.
Friday, Bret. Clin Cancer Res, 2008, vol. 14, No. 2, p. 346.
Roberts, PJ. Oncogene, 2007, vol. 26, pp. 3291-3310.
MedicineNet.com., 2004, Web: <http://www.medterms.com>.
Auto-immune Diseases: MedlinePlus., 2014, Web: <https://wwwnlm.nih.gov/medlineplus/autoimmunediseases.html>.
Neurological Disorders: UCSF Medical Center, 2016, Web: <https://www.ucsfhealth.org/conditions/neurological_disorders/>.
Infections: MedlinePlus, 2016, Web: <https://www.nlm.nih.gov/medlineplus/infections.html>.
WebMD. Inherited Metabolic Disorders.: Types, Causes, Symptoms and Treatments, 2014, Web: <http://www.webmd.com/a-to-z-guides/inherited-metabolic-disorder-types-and-treatments?page=2>.
Myeloproliferative disorders: University of Maryland Medical Center, 2016, Web: <http://umm.edu/health/medical/altmed/condition/myeloproliferative-disorders>.

HETEROCYCLYL COMPOUNDS

CROSS-REFERENCE TO A RELATED APPLICATION

The present application is a continuation of U.S. patent application Ser. No. 14/385,106, filed on Sep. 12, 2014 as the U.S. National Stage application of PCT/IB2013/051915 filed on Mar. 11, 2013, which claims the benefit of Indian Provisional Patent Application No. 0288/KOL/2012, filed on Mar. 14, 2012, the disclosure of each of which is incorporated herein by reference in its entirety.

FIELD OF THE INVENTION

The present invention relates to anticancer compounds, their pharmaceutically acceptable salts, combinations with suitable medicament and pharmaceutical compositions thereof containing one or more such compounds, and methods of treating various cancers.

BACKGROUND OF THE INVENTION

Cancer cells possess certain characteristics that allow them a growth advantage. These include six main alterations in cell physiology such as self-sufficiency in growth signals, insensitivity to growth-inhibitory signals, evasion of apoptosis, indefinite proliferative potential, sustained angiogenesis, tissue invasion and metastasis (Hanahan and Weinberg, Cell, 2000, Vol. 100, 57-70). These changes are triggered by genomic instability and inflammation which generates a microenvironment conducive for tumor growth. In addition to the above mentioned traits, reprogramming of cellular energy metabolism and evasion of immune destruction has also been observed in a majority of cancers.

The enhanced survival in cancer cells is further potentiated by the presence of aberrantly activated signalling pathways. A large majority of cancers are known to have mutations in growth factor signalling cascades that lead to constitutive activation of these pathways. Such constitutive activations has been observed in growth factor receptors which include but are not limited to epidermal growth factor receptor—EGFR, fibroblast growth factor receptor—FGFR, Hepatocyte growth factor receptor—HGF, etc. Furthermore, activating mutations have been reported in certain receptor as well as non receptor tyrosine kinases which include but are not limited to MET receptor tyrosine kinase, EGFR-tyrosine kinase, Bcr-Abl tyrosine kinase, Src tyrosine kinase etc. Activation of Ser-Thr kinases such as Ras and lipid kinases such as PI3-kinases also leads to oncogenesis. Chronic activation of the growth factor/cytokine/hormone-associated signalling leads to activation of immediate downstream components such as Src, Ras, PI3-kinase, etc. These kinases further activate effectors such as MEK, ERK, AKT, eventually leading to activation of transcription factors that endow the cells with a high proliferative potential, improved survival, subversion of metabolic pathways and inhibition of apoptosis (Hanahan and Weinberg, Cell, 2000, Vol. 100, 57-70; Hanahan and Weinberg Cell 2011, Vol. 144, 646-674)

MEK kinase (Mitogen Activated Protein Kinase Kinase (MAPKK)) is an important component of the Ras-RAF-MEK-ERK cell survival pathway. The Ras pathway is activated by binding of growth factors, cytokines, and hormones to their cognate receptors. In cancer cells, this pathway is, however, constitutively activated and leads to increased cancer cell survival, cell proliferation, angiogenesis and metastasis. The tumors that show constitutive activation of the Ras or the MEK kinase include but are not limited to those of the colon, pancreas, breast, brain, ovary, lungs and skin (Sebolt-Leopold and Herrera, Nat. Rev. Cancer 2004, 4 937-947; Fukazawa et al., Mol. Cancer Ther. 2002, Vol. 1, 303-309). Activation of Ras (due to upstream signalling or as a result of activating point mutations in the Ras oncogene) lead to the phosphorylation and activation of Raf kinase that in turn phosphorylate and activate MEK kinase. MEK1/2 kinase phosphorylates and activates the ERK1/2 kinase (also referred to as MAP Kinase) that further phosphorylates and regulates the function of proteins such as Mcl-1, Bim and Bad that are involved in cell survival and apoptosis. Thus, activation of this phosphorylation mediated cascade leads to enhanced cell proliferation, cell survival, decreased cell death that are necessary for initiation and maintenance of the tumorigenic phenotype (Curr. Opin. Invest. Drugs, 2008, 9, 614).

The Ras-Raf-MEK-ERK cascade plays a pivotal role in survival and proliferation of cancer cells. As such, inhibition of this pathway at any of these levels would lead to the inhibition of cancer cell growth, proliferation and survival. Indeed, it has already been reported that inhibition of Ras or Raf leads to inhibition of tumor growth in animal models as well as in cancer patients. However, the success with these inhibitors has been limited to only certain types of cancers (e.g. Sorafenib which inhibits Raf kinase has been approved for renal cell carcinoma). Hence, inhibiting MEK is a novel approach towards controlling this pathway in cancer cells. Moreover, the possibility of designing allosteric inhibitors also allows enhanced selectivity that is crucial for decreasing the toxic effects associated with kinase inhibitors.

The MEK-ERK Pathway is activated in numerous inflammatory conditions (Kyriakis and Avruch, 1996, Vol. 271, No. 40, pp. 24313-24316; Hammaker et al., J. Immunol. 2004, 172, 1612-1618), including rheumatoid arthritis, inflammatory bowel disease and COPD. MEk regulates the biosynthesis of the inflammatory cytokines TNF, IL-6 and IL-1. It has been shown that MEK inhibitors interfere with the production/secretion of these cytokines. Array BioPharma has developed a first-in-class MEK inhibitor (ARRY 438162) and initiated clinical trials in rheumatoid arthritis (RA) patients.

International patent applications WO/2003/053960, WO/2005/023251, WO/2005/121142, WO/2005/051906, WO/2010/121646 describe MEK inhibitors.

BRIEF SUMMARY OF THE INVENTION

The present invention provides anticancer compounds of the general formula (I), their pharmaceutically acceptable salts, combinations with suitable medicament and pharmaceutical compositions thereof and use thereof in treating various cancers.

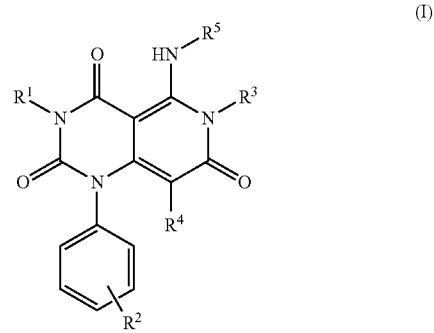

(I)

Wherein, $R^1$-$R^5$ are described in detail below.

The compounds of the present inventions are potent inhibitors of MEK and show tumor regression effect with promisingly less side effects.

DETAILED DESCRIPTION OF THE INVENTION

The present invention relates to heteroaryl compounds of the general formula I, their pharmaceutically acceptable salts, their combinations with suitable medicament and pharmaceutical compositions thereof. The present invention also includes processes of preparation of the compounds and their use in methods of treatment. The compounds are of formula (I) below:

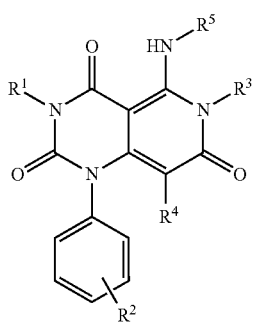

(I)

wherein, $R^1$ is selected from the group consisting of hydrogen, substituted- or unsubstituted-alkyl, substituted- or unsubstituted-cycloalkyl, and substituted- or unsubstituted-heterocyclyl;

$R^2$ is selected from the group consisting of —$R^6$-E, —$SO_2R^7$, and —C(=O)$R^8$;

$R^3$ is selected from the group consisting of hydrogen, substituted- or unsubstituted-alkyl, and substituted- or unsubstituted-cycloalkyl;

$R^4$ is selected from the group consisting of hydrogen, halogen, substituted- or unsubstituted-alkyl, and substituted- or unsubstituted-cycloalkyl;

$R^5$ is substituted- or unsubstituted-aryl, wherein the substituents are selected from the group consisting of $R^a$ and $R^b$;

$R^a$ and $R^b$ are each independently selected from the group consisting of hydrogen, halogen and haloalkyl;

$R^6$ is selected from the group consisting of direct bond, —[C($R^c$)$R^d$]$_n$$NR^9$—, —[C($R^c$)$R^d$]$_n$O—, —NHC(=O)[C($R^c$)$R^d$]$_p$—, —S(O)$_2$NH—, —NHC(=O)[C$R^c$($R^d$)]$NR^9$—, —NHC(=O)[C$R^c$($R^d$)]O—, and —NHS(O)$_2$—;

$R^c$ and $R^d$ are each independently selected from the group consisting of hydrogen and substituted- or unsubstituted alkyl;

E is four membered heterocyclic ring substituted- or unsubstituted—with alkyl, halogen, —C(=O)O$R^e$ and —O$R^e$;

$R^e$ is selected from the group consisting of hydrogen, substituted- or unsubstituted-alkyl and substituted or unsubstituted cycloalkyl;

$R^7$ is selected from the group consisting of substituted- or unsubstituted-cycloalkyl, and substituted- or unsubstituted-cycloalkenyl;

$R^8$ is selected from the group consisting of substituted- or unsubstituted-alkyl, substituted- or unsubstituted-alkenyl, substituted- or unsubstituted-alkynyl, substituted- or unsubstituted-cycloalkyl, and substituted- or unsubstituted-cycloalkenyl;

$R^9$ is selected from the group consisting of hydrogen, substituted- or unsubstituted-alkyl, substituted- or unsubstituted-alkenyl, substituted- or unsubstituted-alkynyl, substituted- or unsubstituted-cycloalkyl and substituted or unsubstituted-cycloalkenyl;

n is an integer selected from the group consisting of 0, 1 and 2;

p is an integer selected from 0 and 1;

when the alkyl group and alkenyl group is substituted, the alkyl group and alkenyl group is substituted with 1 to 4 substituents independently selected from the group consisting of oxo, halogen, nitro, cyano, perhaloalkyl, cycloalkyl, aryl, heteroaryl, heterocyclyl, —$OR^{10b}$, —$SO_2R^{10a}$, —C(=O)$OR^{10a}$, —OC(=O)$R^{10a}$, —C(=O)N(H)$R^{10}$, —$OR^{10a}$, —C(=O)N(alkyl)$R^{10}$, —N(H)C(=O)$R^{10a}$, —N(H)$R^{10}$, —N(alkyl)$R^{10}$—N(H)C(=O)N(H)$R^{10}$, —N(H)C(=O)N(alkyl)$R^{10}$, —NH—$SO_2$-alkyl, and —NH—$SO_2$-cycloalkyl;

when the cycloalkyl group and cycloalkenyl group is substituted, the cycloalkyl group and cycloalkenyl group is substituted with 1 to 3 substituents independently selected from the group consisting of oxo, halogen, nitro, cyano, alkyl, alkenyl, perhaloalkyl, aryl, heteroaryl, heterocyclyl, —$OR^{10b}$, —$SO_2R^{10a}$, —C(=O)$R^{10a}$, —C(=O)$OR^{10a}$, —OC(=O)$R^{10a}$, —C(=O)N(H)$R^{10}$, —C(=O)N(alkyl)$R^{10}$, —N(H)C(=O)$R^{10a}$, —N(H)$R^{10}$, —N(alkyl)$R^{10}$, —N(H)C(=O)N(H)$R^{10}$, and —N(H)C(=O)N(alkyl)$R^{10}$, —NH—$SO_2$-alkyl, and —NH—$SO_2$-cycloalkyl;

when the aryl group is substituted, the aryl group is substituted with 1 to 3 substituents independently selected from the group consisting of halogen, nitro, cyano, hydroxy, alkyl, alkenyl, perhaloalkyl, cycloalkyl, cycloalkenyl, heterocycle, —O-alkyl, —O-perhaloalkyl, —N(alkyl)alkyl, —N(H)alkyl, —$NH_2$, —$SO_2$-alkyl, —$SO_2$-perhaloalkyl, —N(alkyl)C(=O)alkyl, —N(H)C(=O)alkyl, —C(=O)N(alkyl)alkyl, —C(=O)N(H)alkyl, —C(=O)$NH_2$, —$SO_2$N(alkyl)alkyl, —$SO_2$N(H)alkyl, —$SO_2NH_2$, —NH—$SO_2$-alkyl, and —NH—$SO_2$-cycloalkyl;

when the heteroaryl group is substituted, the heteroaryl group is substituted with 1 to 3 substituents independently selected from the group consisting of halogen, nitro, cyano, hydroxy, alkyl, alkenyl, perhaloalkyl, cycloalkyl, cycloalkenyl, heterocycle, —O-alkyl, O-perhaloalkyl, —N(alkyl)alkyl, —N(H)alkyl, —$NH_2$, —$SO_2$-alkyl, —$SO_2$-perhaloalkyl, —N(alkyl)C(=O)alkyl, —N(H)C(=O)alkyl, —C(=O)N(alkyl)alkyl, —C(=O)N(H)alkyl, —C(=O)$NH_2$, —$SO_2$N(alkyl)alkyl, —$SO_2$N(H)alkyl, —$SO_2NH_2$, —NH—$SO_2$-alkyl, and —NH—$SO_2$-cycloalkyl;

when the heterocyclyl group is substituted, the heterocyclyl group is substituted with 1 to 3 substituents. When the substituents are on a ring carbon of the 'heterocycle', the substituents are independently selected from the group consisting of halogen, nitro, cyano, oxo, alkyl, alkenyl, perhaloalkyl, cycloalkyl, cycloalkenyl, aryl, heteroaryl, heterocyclyl, —$OR^{10b}$, —C(=O)$OR^{10a}$, —OC(=O)$R^{10a}$, —C(=O)N(H)$R^{10}$, —C(=O)N(alkyl)$R^{10}$, —N(H)C(=O)$R^{10a}$, —N(H)$R^{10}$, —N(alkyl)$R^{10}$, —N(H)C(=O)N(H)$R^{10}$, —N(H)C(=O)N(alkyl)$R^{10}$. When the heterocyclic group is substituted on a ring nitrogen of the 'heterocycle', the substituents are selected from the group consisting of alkyl, alkenyl, cycloalkyl, cycloalkenyl, aryl, heteroaryl, —$SO_2R^{10a}$, —C(=O)$R^{10a}$, C(=O)$OR^{10a}$, —C(=O)N(H)$R^{10}$, —C(=O)N(alkyl)$R^{10}$, —NH—$SO_2$-alkyl, and —NH—$SO_2$-cycloalkyl;

$R^{10}$ is selected from the group consisting of hydrogen, alkyl, alkenyl, cycloalkyl, cycloalkenyl, aryl, heteroaryl, and heterocyclyl;

$R^{10a}$ is selected from the group consisting of alkyl, alkenyl, perhaloalkyl, cycloalkyl, cycloalkenyl, aryl, heteroaryl, and heterocyclyl;

$R^{10b}$ is selected from the group consisting of hydrogen, alkyl, alkenyl, perhaloalkyl, cycloalkyl, cycloalkenyl, aryl, heteroaryl, and heterocyclyl;

In certain embodiments, $R^1$ is selected from the group consisting of hydrogen, substituted- or unsubstituted-alkyl, and substituted- or unsubstituted-cycloalkyl.

In other embodiments, $R^1$ is selected from the group consisting of hydrogen, methyl and cyclopropyl.

In certain embodiments, $R^3$ is substituted- or unsubstituted-alkyl.

In other embodiments, $R^3$ is methyl.

In certain embodiments, $R^4$ is substituted- or unsubstituted-alkyl.

In other embodiments, $R^4$ is methyl.

In certain embodiments, $R^5$ is substituted- or unsubstituted-phenyl, wherein the substituents are independently selected from $R^a$ and $R^b$.

In certain embodiments, $R^a$ and $R^b$ are particularly selected from hydrogen, halogen and haloalkyl.

In other embodiments, $R^a$ and $R^b$ are independently fluorine or iodine.

In certain embodiments, $R^6$ is selected from the group consisting of direct bond, $-[C(R^c)R^d]_nNR^9$, $-[C(R^c)R^d]_nO-$, and $-NHC(=O)[C(R^c)R^d]_p-$.

In other embodiments, $R^6$ is selected from the group consisting of direct bond, $-NH-$, $-O-$, $-CH_2O-$, and $-NHC(=O)-$.

In certain embodiments, E is selected from the group consisting of substituted- or unsubstituted-3-oxetane, 1-azetidine, 1-azetidine-2-one and 3-azetidine; wherein substituents are independently selected from methyl, fluoro, $-C(=O)OR^e$, and $-OR^e$.

In certain embodiments, $R^e$ is selected from hydrogen and substituted- or unsubstituted-alkyl.

In other embodiments, $R^e$ is selected from hydrogen, tert-butyl, and $-CH_2C(=O)NH_2$.

In certain embodiments, $R^7$ is substituted- or unsubstituted-cycloalkyl.

In other embodiments, $R^7$ is cyclopropyl.

In certain embodiments, $R^8$ is substituted- or unsubstituted-cycloalkyl.

In other embodiments, $R^8$ is cyclopropyl.

In certain embodiments, $R^9$ is hydrogen.

In one embodiment, the present invention is a compound of formula Ia:

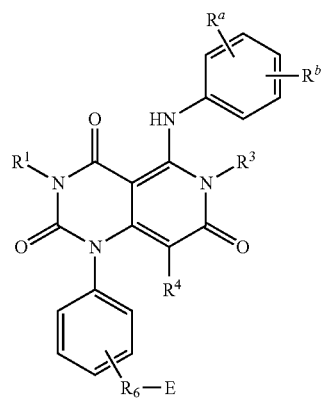

(Ia)

wherein,
$R^1$, $R^3$, $R^4$, $R^6$, E, $R^a$ and $R^b$ are as defined in formula (I).

In another embodiment, the present invention is a compound of formula (Ib):

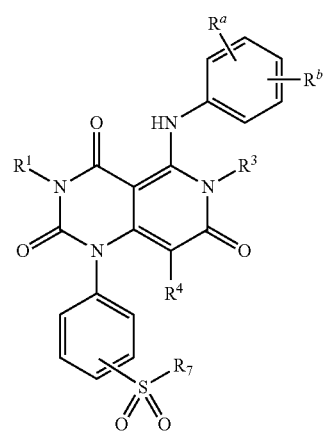

(Ib)

Wherein;
$R^1$, $R^3$, $R^4$, $R^7$, $R^a$ and $R^b$ are as defined in formula (I);

In another embodiment, the present invention is a compound of formula (Ic):

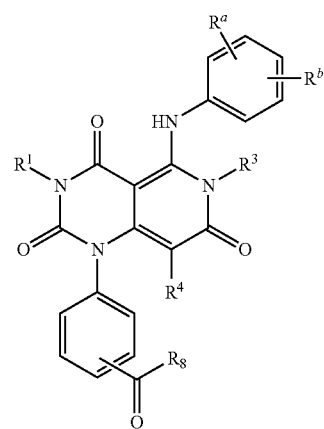

(Ic)

Wherein:
$R^1$, $R^3$, $R^4$, $R^8$, $R^a$ and $R^b$ are as defined in formula (I).

General terms used in any of the formulae herein can be defined as follows; however, the meaning stated should not be interpreted as limiting the scope of the term per se.

The term "alkyl", as used herein, means a straight chain or branched hydrocarbon containing from 1 to 20 carbon atoms. Preferably the alkyl chain may contain 1 to 10 carbon atoms. More preferably alkyl chain may contain up to 6 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

The term "alkenyl" as used herein, means an 'alkyl' group as defined hereinabove containing 2 to 20 carbon atoms and containing at least one double bond. Representative examples of alkenyl include, but are not limited to, pent-2-enyl, hex-3-enyl, allyl, vinyl, and the like.

'Alkyl', 'alkenyl' as defined hereinabove may be substituted with one or more substituents selected independently from the group comprising of oxo, halogen, nitro, cyano, haloalkyl, cycloalkyl, aryl, heteroaryl, heterocyclyl, —OR$^{10b}$, —SO$_2$R$^{10a}$, —C(=O)R$^{10a}$, —C(=O)OR$^{10a}$, —OC(=O)R$^{10a}$, —C(=O)N(H)R$^{10}$, —C(=O)N(alkyl)R$^{10}$, —N(H)C(=O)R$^{10a}$, —N(H)R$^{10}$, —N(alkyl)R$^{10}$, —N(H)C(=O)N(H)R$^{10}$, —N(H)C(=O)N(alkyl)R$^{10}$, —NH—SO$_2$-alkyl and —NH—SO$_2$-cycloalkyl; wherein, R$^{10}$ is selected from the group consisting of hydrogen, alkyl, alkenyl, cycloalkyl, cycloalkenyl, aryl, heteroaryl, and heterocyclyl; R$^{10a}$ is selected from the group consisting of alkyl, alkenyl, haloalkyl, perhaloalkyl, cycloalkyl, cycloalkenyl, aryl, heteroaryl, heterocyclyl; R$^{10b}$ is selected from the group consisting of hydrogen, alkyl, alkenyl, haloalkyl, perhaloalkyl, cycloalkyl, cycloalkenyl, aryl, heteroaryl, and heterocyclyl.

The term "haloalkyl" means alkyl, as the case may be, substituted with one or more halogen atoms, where alkyl groups are as defined above. The term "halo" is used herein interchangeably with the term "halogen" and means F, Cl, Br or I. Examples of "haloalkyl" include but are not limited to trifluoromethyl, difluoromethyl, 2,2,2-trifluoroethyl, pentafluoroethyl, pentachloroethyl, 4,4,4-trifluorobutyl, 4,4-difluorocyclohexyl, chloromethyl, dichloromethyl, trichloromethyl, 1-bromoethyl and the like. The term "perhaloalkyl" group is defined hereinabove wherein all the hydrogen atoms of the said alkyl group are substituted with halogen, exemplified by trifluoromethyl, pentafluoroethyl and the like.

The term "cycloalkyl" as used herein, means a monocyclic, bicyclic, or tricyclic non-aromatic ring system containing from 3 to 14 carbon atoms, preferably monocyclic cycloalkyl ring containing 3 to 6 carbon atoms. Examples of monocyclic ring systems include cyclopropyl, cyclobutyl, cyclopentyl, cyclohexyl, cycloheptyl, and cyclooctyl. Bicyclic ring systems are also exemplified by a bridged monocyclic ring system in which two non-adjacent carbon atoms of the monocyclic ring are linked by an alkylene bridge. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane, bicyclo[3.3.2]decane, bicyclo[3.1.0] hexane, bicyclo[410]heptane, bicyclo[3.2.0]heptanes, octahydro-1H-indene. Tricyclic ring systems are also exemplified by a bicyclic ring system in which two non-adjacent carbon atoms of the bicyclic ring are linked by a bond or an alkylene bridge. Representative examples of tricyclic-ring systems include, but are not limited to, tricyclo[3.3.1.0$^{3.7}$]nonane and tricyclo[3.3.1.1$^{3.7}$]decane (adamantane). The term cycloalkyl also include spiro systems wherein one of the ring is annulated on a single carbon atom such ring systems are exemplified by spiro[2.5]octane, spiro[4.5]decane, spiro[bicyclo[4.1.0]heptane-2,1'-cyclopentane], hexahydro-2'H-spiro[cyclopropane-1,1'-pentalene].

The term "cycloalkenyl" as used herein, means a cycloalkyl group as defined above containing at least one double bond.

'cycloalkyl' and 'cycloalkenyl' as defined hereinabove may be substituted- or unsubstituted—with one or more substituents selected independently from the group consisting of oxo, halogen, nitro, cyano, hydroxyl, hydroxyalkyl, alkyl, alkenyl, perhaloalkyl, aryl, heteroaryl, heterocyclyl, —OR$^{10b}$, —SO$_2$R$^{10a}$, —C(=O)R$^{10a}$, —C(=O)OR$^{10a}$, —OC(=O)R$^{10a}$, —C(=O)N(H)R$^{10}$, —C(=O)N(alkyl)R$^{10}$, —N(H)C(=O)R$^{10a}$, —N(H)R$^{10}$, —N(alkyl)R$^{10}$, —N(H)C(=O)N(H)R$^{10}$, —N(H)C(=O)N(alkyl)R$^{10}$, —NH—SO$_2$-alkyl and —NH—SO$_2$-cycloalkyl; wherein, R$^{10}$ is selected from the group consisting of hydrogen, alkyl, alkenyl, cycloalkyl, cycloalkenyl, aryl, heteroaryl, and heterocyclyl; R$^{10a}$ is selected from the group consisting of alkyl, alkenyl, perhaloalkyl, cycloalkyl, cycloalkenyl, aryl, heteroaryl, heterocyclyl; R$^{10b}$ is selected from the group consisting of hydrogen, alkyl, alkenyl, perhaloalkyl, cycloalkyl, cycloalkenyl, aryl, heteroaryl, and heterocyclyl.

The term "aryl" refers to a monovalent monocyclic, bicyclic or tricyclic aromatic hydrocarbon ring system. Examples of aryl groups include phenyl, naphthyl, anthracenyl, fluorenyl, indenyl, azulenyl, and the like. Aryl group also include partially saturated bicyclic and tricyclic aromatic hydrocarbons such as tetrahydro-naphthalene. The said aryl group also includes aryl rings fused with heteroaryl or heterocyclic rings such as 2,3-dihydro-benzo[1,4]dioxin-6-yl; 2,3-dihydro-benzo[1,4]dioxin-5-yl; 2,3-dihydro-benzofuran-5-yl; 2,3-dihydro-benzofuran-4-yl; 2,3-dihydro-benzofuran-6-yl; 2,3-dihydro-benzofuran-6-yl; 2,3-dihydro-1H-indol-5-yl; 2,3-dihydro-1H-indol-4-yl; 2,3-dihydro-1H-indol-6-yl; 2,3-dihydro-1H-indol-7-yl; benzo[1,3]dioxol-4-yl; benzo[1,3]dioxol-5-yl; 1,2,3,4-tetrahydroquinolinyl; 1,2,3,4-tetrahydroisoquinolinyl; 2,3-dihydrobenzothien-4-yl, 2-oxoindolin-5-yl.

Aryl as defined hereinabove may be substituted- or unsubstituted—with one or more substituents selected independently from the group consisting of halogen, nitro, cyano, hydroxy, alkyl, alkenyl, perhaloalkyl, cycloalkyl, cycloalkenyl, heterocycle, —O-alkyl, —O— perhaloalkyl, —N(alkyl)alkyl, —N(H)alkyl, —NH$_2$, —SO$_2$-alkyl, —SO$_2$-perhaloalkyl, —N(alkyl)C(=O)alkyl, —N(H)C(=O)alkyl, —C(=O)N(alkyl)alkyl, —C(=O)N(H)alkyl, —C(=O)NH$_2$, —SO$_2$N(alkyl)alkyl, —SO$_2$N(H)alkyl, —SO$_2$NH$_2$, —NH—SO$_2$-alkyl and —NH—SO$_2$-cycloalkyl;

The term "heteroaryl" refers to a 5-14 membered monocyclic, bicyclic, or tricyclic ring system having 1-4 ring heteroatoms selected from O, N, or S, and the remainder ring atoms being carbon (with appropriate hydrogen atoms unless otherwise indicated), wherein at least one ring in the ring system is aromatic. Heteroaryl groups may be substituted—or unsubstituted—with one or more substituents. In one embodiment, 0, 1, 2, 3, or 4 atoms of each ring of a heteroaryl group may be substituted by a substituent. Examples of heteroaryl groups include pyridyl, 1-oxopyridyl, furanyl, thienyl, pyrrolyl, oxazolyl, oxadiazolyl, imidazolyl, thiazolyl, isoxazolyl, quinolinyl, pyrazolyl, isothiazolyl, pyridazinyl, pyrimidinyl, pyrazinyl, triazinyl. triazolyl, thiadiazolyl, isoquinolinyl, benzoxazolyl, benzofuranyl, indolizinyl, imidazopyridyl, tetrazolyl, benzimidazolyl, benzothiazolyl, benzothiadiazolyl, benzoxadiazolyl, indolyl, azaindolyl, imidazopyridyl, quinazolinyl, purinyl, pyrrolo[2,3]pyrimidinyl, pyrazolo[3,4]pyrimidinyl, and benzo(b)thienyl, 2,3-thiadiazolyl, 1H-pyrazolo[5,1-c]-1,2,4-triazolyl, pyrrolo[3,4-d]-1,2,3-triazolyl, cyclopentatriazolyl, 3H-pyrrolo[3,4-c] isoxazolyl and the like.

Heteroaryl as defined hereinabove may be substituted- or unsubstituted—with one or more substituents selected independently from the group consisting of halogen, nitro, cyano, hydroxy, alkyl, alkenyl, perhaloalkyl, cycloalkyl, cycloalkenyl, heterocycle, —O-alkyl, O-perhaloalkyl, —N(alkyl)alkyl, —N(H)alkyl, —NH$_2$, —SO$_2$-alkyl, —SO$_2$-perhaloalkyl, —N(alkyl)C(=O)alkyl, —N(H)C(=O)alkyl, —C(=O)N(alkyl)alkyl, —C(=O)N(H)alkyl, —C(=O)NH$_2$, —SO$_2$N(alkyl)alkyl, —SO$_2$N(H)alkyl, —SO$_2$NH$_2$, —NH—SO$_2$-alkyl and —NH—SO$_2$-cycloalkyl;

The term "heterocycle" or "heterocyclic" as used herein, means a 'cycloalkyl' group wherein one or more of the carbon atoms replaced by —O—, —S—, —S(O₂)—, —S(O)—, —N(R′′′)—, —Si(R′′′)R′′—, wherein, R′′′ and R′′ are independently selected from the group consisting of hydrogen, alkyl, alkenyl, alkynyl, aryl, heteroaryl, cycloalkyl, and heterocyclyl. The heterocycle may be connected to the parent molecular moiety through any carbon atom or any nitrogen atom contained within the heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl. oxadiazolidinyl, oxazolinyl, oxazolidinyl, piperazinyl, piperidinyl, pyranyl, pyrazolinyl, pyrazolidinyl. pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1.1-dioxidothiomorpholinyl (thiomorpholine sulfone). thiopyranyl, and trithianyl. Representative examples of bicyclic heterocycle include, but are not limited to 1,3-benzodioxolyl, 1,3-benzodithiolyl, 2,3-dihydro-1,4-benzodioxinyl, 2,3-dihydro-1-benzofuranyl, 2,3-dihydro-1-benzothienyl, 2,3-dihydro-1H-indolyl and 1,2,3,4-tetrahydroquinolinyl. The term heterocycle also include bridged heterocyclic systems such as azabicyclo[3.2.1]octane, azabicyclo[3.3.1]nonane and the like.

Heterocyclyl group may be substituted- or unsubstituted- on ring carbons with one or more substituents selected independently from the group consisting of: halogen, nitro, cyano, oxo, alkyl, alkenyl, perhaloalkyl, cycloalkyl, cycloalkenyl, aryl, heteroaryl, heterocyclyl, —OR$^{10b}$, —C(=O)OR$^{10a}$, —OC(=O)R$^{10a}$, —C(=O)N(H)R$^{10}$, —C(=O)N(alkyl)R$^{10}$, —N(H)C(=O)R$^{10a}$, —N(H)R$^{10}$, —N(alkyl)R$^{10}$, —N(H)C(=O)N(H)R$^{10}$, —N(H)C(=O)N(alkyl)R$^{10}$; the substituents on ring nitrogen of 'heterocycle' is selected from alkyl, alkenyl, cycloalkyl, cycloalkenyl, aryl, heteroaryl, —SO₂R$^{10a}$, —C(=O)R$^{10a}$, C(=O)OR$^{10a}$, —C(=O)N(H)R$^{10}$, —C(=O)N(alkyl)R$^{10}$, —NH—SO₂-alkyl and —NH—SO₂-cycloalkyl; R$^{10a}$ is selected from alkyl, alkenyl, perhaloalkyl, cycloalkyl, cycloalkenyl, aryl, heteroaryl, heterocyclyl; R$^{10b}$ is selected from hydrogen, alkyl, alkenyl, perhaloalkyl, cycloalkyl, cycloalkenyl, aryl, heteroaryl, and heterocyclyl.

The term 'oxo' means a divalent oxygen (=O) attached to the parent group. For example oxo attached to carbon forms a carbonyl, oxo substituted on cyclohexane forms a cyclohexanone, and the like.

The term 'annulated' means the ring system under consideration is either annulated with another ring at a carbon atom of the cyclic system or across a bond of the cyclic system as in the case of fused or spiro ring systems.

The term 'bridged' means the ring system under consideration contain an alkylene bridge having 1 to 4 methylene units joining two non adjacent ring atoms.

It should be understood that the formulas (I), (Ia), (Ib) and (Ic) structurally encompasses all tautomers and pharmaceutically acceptable salts that may be contemplated from the chemical structure of the genera described herein.

A compound its racemates, tautomers and pharmaceutically acceptable salt thereof as described hereinabove wherein the compound of general formula I, (Ia), (Ib) and (Ic) is selected from the group consisting of:

1-(3-(cyclopropylsulfonyl)phenyl)-5-((2-fluoro-4-iodophenyl)amino)-6,8-dimethyl pyrido [4,3-d]pyrimidine-2,4,7 (1H,3H,6H)-trione (Compound 1)

3-cyclopropyl-5-((2-fluoro-4-iodophenyl)amino)-1-(3-(3-hydroxyazetidin-1-yl)phenyl)-6,8-dimethylpyrido[4,3-d]pyrimidine-2,4,7(1H,3H,6H)-trione (Compound 2)

3-cyclopropyl-1-(3-(cyclopropylsulfonyl)phenyl)-5-((2-fluoro-4-iodophenyl)amino)-6,8-dimethylpyrido[4,3-d]pyrimidine-2,4,7(1H,3H,6H)-trione (Compound 3)

3-cyclopropyl-5-((2-fluoro-4-iodophenyl)amino)-6,8-dimethyl-1-(3-(2-oxoazetidin-1-yl)phenyl)pyrido[4,3-d]pyrimidine-2,4,7(1H,3H,6H)-trione (Compound 4)

3-cyclopropyl-5-((2-fluoro-4-iodophenyl)amino)-6,8-dimethyl-1-(3-(oxetan-3-ylamino) phenyl)pyrido[4,3-d]pyrimidine-2,4,7(1H,3H,6H)-trione (Compound 5)

tert-butyl 3-((3-(3-cyclopropyl-5-((2-fluoro-4-iodophenyl)amino)-6,8-dimethyl-2,4,7-trioxo-3,4,6,7-tetrahydro-pyrido[4,3-d]pyrimidin-1 (2H)-yl)phenyl)carbamoyl) azetidine-1-carboxylate (Compound 6)

3-cyclopropyl-5-((2-fluoro-4-iodophenyl)amino)-6,8-dimethyl-1-(3-(oxetan-3-yloxy) phenyl)pyrido[4,3-d]pyrimidine-2,4,7(1H,3H,6H)-trione (Compound 7)

1-(3-(azetidin-1-yl)phenyl)-3-cyclopropyl-5-((2-fluoro-4-iodophenyl)amino)-6,8-dimethyl pyrido[4,3-d]pyrimidine-2,4,7(1H,3H,6H)-trione (Compound 8)

3-cyclopropyl-5-((2-fluoro-4-iodophenyl)amino)-1-(3-(3-hydroxyoxetan-3-yl)phenyl)-6,8-dimethylpyrido[4,3-d]pyrimidine-2,4,7(1H,3H,6H)-trione (Compound 9)

N-(3-(3-cyclopropyl-5-((2-fluoro-4-iodophenyl)amino)-6,8-dimethyl-2,4,7-trixo-3,4,6,7-tetrahydropyrido[4,3-d]pyrimidin-1(2H)-yl)phenyl)-3-methyloxetane-3-carboxamide (Compound 10)

1-(3-(cyclopropanecarbonyl)phenyl)-3-cyclopropyl-5-((2-fluoro-4-iodophenyl)amino)-6,8-dimethylpyrido[4,3-d]pyrimidine-2,4,7(1H,3H,6H)-trione (Compound 11)

1-(3-(cyclopropylsulfonyl)phenyl)-5-((2-fluoro-4-iodophenyl)amino)-3,6,8-trimethyl pyrido[4,3-d]pyrimidine-2,4,7(1H,3H,6H)-trione (Compound 12)

5-((2-fluoro-4-iodophenyl)amino)-3,6,8-trimethyl-1-(3-((oxetan-3-yloxy)methyl) phenyl)pyrido[4,3-d]pyrimidine-2,4,7(1H,3H,6H)-trione (Compound 13)

5-((2-fluoro-4-iodophenyl)amino)-1-(3-(3-hydroxyoxetan-3-yl)phenyl)-3,6,8-trimethylpyrido[4,3-d]pyrimidine-2,4,7(1H,3H,6H)-trione (Compound 14)

5-((2-fluoro-4-iodophenyl)amino)-3,6,8-trimethyl-1-(3-(oxetan-3-yloxy)phenyl) pyrido[4,3-d]pyrimidine-2,4,7(1H,3H,6H)-trione (Compound 15)

1-(3-(azetidin-1-yl)phenyl)-5-((2-fluoro-4-iodophenyl)amino)-3,6,8-trimethylpyrido[4,3-d]pyrimidine-2,4,7 (1H,3H,6H)-trione (Compound 16)

5-((2-fluoro-4-iodophenyl)amino)-3,6,8-trimethyl-1-(3-(oxetan-3-ylamino)phenyl) pyrido[4,3-d]pyrimidine-2,4,7 (1H,3H,6H)-trione (Compound 17)

N-(3-(5-((2-fluoro-4-iodophenyl)amino)-3,6,8-trimethyl-2,4,7-trioxo-3,4,6,7-tetrahydropyrido[4,3-d]pyrimidin-1 (2H)-yl)phenyl)-3-methyloxetane-3-carboxamide (Compound 18)

2-((1-(3-(5-((2-fluoro-4-iodophenyl)amino)-3,6,8-trimethyl-2,4,7-trioxo-3,4,6,7-tetrahydropyrido[4,3-d]pyrimidin-1(2H)-yl)phenyl)azetidin-3-yl)oxy)acetamide (Compound 19)

5-((2-fluoro-4-iodophenyl)amino)-1-(3-(3-fluorooxetan-3-yl)phenyl)-3,6,8-trimethylpyrido[4,3-d]pyrimidine-2,4,7 (1H,3H,6H)-trione (Compound 20)

N-(3-(3-cyclopropyl-5-((2-fluoro-4-iodophenyl)amino)-6,8-dimethyl-2,4,7-trioxo-3,4,6,7-tetrahydropyrido[4,3-d]pyrimidin-1 (2H)-yl)phenyl)azetidine-3-carboxamide (Compound 21)

The present disclosure provides a method for inhibiting MEK enzymes comprising contacting said MEK enzyme with a composition comprising a compound of I, Ia, Ib, Ic, their tautomeric forms or their pharmaceutically acceptable salts, sufficient to inhibit said enzyme, wherein said enzyme inhibited MEK kinase, which occurs within cell.

The invention also provides a method of treatment of a MEK mediated disorder in an individual suffering from said disorder, comprising administering to said individual an effective amount of a composition comprising a compound of formula I, Ia, Ib, Ic, their tautomeric forms or their pharmaceutically acceptable salts. The said method of treatment may also be combined with an additional therapy such as radiation therapy, chemotherapy, or combination thereof.

MEK mediated disorders as stated above include inflammatory diseases, infections, autoimmune disorders, stroke, ischemia, cardiac disorder, neurological disorders, fibrogenetic disorders, proliferative disorders, hyperproliferative disorders, tumors, leukemias, neoplasms, cancers, carcinomas, metabolic diseases and malignant diseases.

The invention further provides a method for the treatment or prophylaxis of a proliferative disease in an individual comprising administering to said individual an effective amount of a composition comprising a compound of formula I, Ia, Ib, Ic, their tautomeric forms or their pharmaceutically acceptable salts. The proliferative disease includes cancer, psoriasis, restenosis, autoimmune disease, or atherosclerosis.

The invention also provides a method for the treatment or prophylaxis of an inflammatory disease in an individual comprising administering to said individual an effective amount of a composition comprising a compound of formula I, Ia, Ib, Ic, their tautomeric forms or their pharmaceutically acceptable salts. The inflammatory disease includes rheumatoid arthritis or multiple sclerosis.

The invention also provide a method for degrading, inhibiting the growth of or killing cancer cells comprising contacting the cells with an amount of a composition effective to degrade, inhibit the growth of or kill cancer cells, the composition comprising a compound of formula I, Ia, Ib, Ic, their tautomeric forms or their pharmaceutically acceptable salts.

The invention also provide a method of inhibiting tumor size increase, reducing the size of a tumor, reducing tumor proliferation or preventing tumor proliferation in an individual in need thereof comprising administering to said individual an effective amount of a composition to inhibit tumor size increase, reduce the size of a tumor, reduce tumor proliferation or prevent tumor proliferation, the composition comprising a compound of formula I, Ia, Ib, Ic, their tautomeric forms or their pharmaceutically acceptable salts.

The MEK-ERK pathway is activated in numerous inflammatory conditions (Kyriakis and Avruch 1996, Vol. 271, No. 40, pp. 24313-24316; Hammaker et al., J Immunol 2004; 172; 1612-1618), including rheumatoid arthritis, inflammatory bowel disease and COPD. MEK regulates the biosynthesis of the inflammatory cytokines TNF, IL-6 and IL-1. It has been shown that MEK inhibitors interfere with the production/secretion of these cytokines.

The present invention describes the inhibitors of MEK kinase for treatment of disorders that are driven by hyperactivation, abnormal activation, constitutive activation, gain-of-function mutation of the MEK kinase and/or its substrate kinases that include but are not limited to ERK. Such disorders encompass hyperproliferative disorders that include but are not limited to psoriasis, keloids, hyperplasia of the skin, benign prostatic hyperplasia (BPH), solid tumors such as cancers of the respiratory tract (including but not limited to small cell and non-small cell lung carcinomas), brain (including but not limited to glioma, medulloblastoma, ependymoma, neuroectodermal and pineal tumors), breast (including but not limited to invasive ductal carcinoma, invasive lobular carcinoma, ductal- and lobular carcinoma in situ), reproductive organs (including but not limited to prostate cancer, testicular cancer, ovarian cancer, endometrial cancer, cervical cancer, vaginal cancer, vulvar cancer, and sarcoma of the uterus), digestive tract (including but not limited to esophageal, colon, colorectal, gastric, gall blabber, pancreatic, rectal, anal, small intestine and salivary gland cancers), urinary tract (including but not limited to bladder, ureter, kidney, renal, urethral and papillary renal cancers), eye (including but not limited to intraocular melanoma, and retinoblastoma), liver (including but not limited to hepatocellular carcinoma, and cholangiocarcinoma), skin (including but not limited to melanoma, squamous cell carcinoma, Kaposi's sarcoma, Merkel cell skin cancer, non-melanoma skin cancer), head and neck (including but not limited to laryngeal, nasopharyngeal, hypopharyngeal, oropharyngeal cancer, lip and oral cavity cancer and squamous cell cancer), thyroid, parathyroid, and their metastases. The hyperproliferative disorders also include, leukemias (including but not limited to acute lymphoblastic leukemia, acute myeloid leukemia, chronic melogenous leukemia, chronic lymphocytic leukemia, and hairy cell leukemia), sarcomas (including but not limited to soft tissue sarcoma, osteosarcoma, lymphosarcoma, rhabdomyosarcoma), and lymphomas (including but not limited to non-Hodgkin's lymphoma, AIDS-related lymphoma, cutaneous T cell lymphoma, Burkitt's lymphoma, Hodgkin's disease, and lymphoma of the central nervous system).

The present invention describes the inhibitors of MEK kinase for treatment of certain disorders involving aberrant regulation of the mitogen extracellular kinase activity including but not limited to hepatomegaly, heart failure, cardiomegaly, diabetes, stroke, Alzheimer's disease, cystic fibrosis, septic shock or asthma.

The present invention describes the inhibitors of MEK kinase for treatment of diseases and disorders associated with aberrant, abnormal and/or excessive angiogenesis. Such disorders associated with angiogenesis include but are not limited to, tumor growth and metastases, ischemic retinal vein occlusion, diabetic retinopathy, macular degeneration, neovascular glaucoma, psoriasis, inflammation, rheumatoid arthritis, vascular graft restenosis, restenosis and in-stent restenosis.

The compounds mentioned in this invention can be used as a single (sole) therapeutic agent or in combination with other active agents, including chemotherapeutic agents and anti-inflammatory agents. Such combinations include but are not limited to combining the MEK kinase inhibitors with anti-mitotic agents, anti-antiangiogenic agents, alkylating agents, anti-hyperproliferative agents, antimetabolites, DNA-intercalating agents, cell cycle inhibitors, kinase inhibitors, growth factor inhibitors, enzyme inhibitors, topoisomerase inhibitors, biological response modifiers or anti-hormones.

The term 'room temperature' denotes any temperature ranging between about 20° C. to about 40° C., except and otherwise it is specifically mentioned in the specification.

The intermediates and the compounds of the present invention may be obtained in pure form in a manner known per se, for example, by distilling off the solvent in vacuum and re-crystallizing the residue obtained from a suitable solvent, such as pentane, diethyl ether, isopropyl ether, chloroform, dichloromethane, ethyl acetate, acetone or their combinations or subjecting it to one of the purification methods, such as column chromatography (e.g., flash chromatography) on a suitable support material such as alumina or silica gel using eluent such as dichloromethane, ethyl acetate, hexane, methanol, acetone and their combinations. Preparative LC-MS method is also used for the purification of molecules described herein.

Salts of compound of formula I can be obtained by dissolving the compound in a suitable solvent, for example in a chlorinated hydrocarbon, such as methyl chloride or chloroform or a low molecular weight aliphatic alcohol, for example, ethanol or isopropanol, which was then treated with the desired acid or base as described in Berge S. M. et al. "Pharmaceutical Salts, a review article in Journal of Pharmaceutical sciences volume 66, page 1-19 (1977)" and in handbook of pharmaceutical salts properties, selection, and use by P. H. Einrich Stahland Camille G. wermuth, Wiley-VCH (2002). Lists of suitable salts can also be found in *Remington's Pharmaceutical Sciences,* 18th ed., Mack Publishing Company, Easton, Pa., 1990, p. 1445, and *Journal of Pharmaceutical Science,* 66, 2-19 (1977). For example, the salt can be of an alkali metal (e.g., sodium or potassium), alkaline earth metal (e.g., calcium), or ammonium.

The compound of the invention or a composition thereof can potentially be administered as a pharmaceutically acceptable acid-addition, base neutralized or addition salt, formed by reaction with inorganic acids, such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base, such as sodium hydroxide, potassium hydroxide. The conversion to a salt is accomplished by treatment of the base compound with at least a stoichiometric amount of an appropriate acid. Typically, the free base is dissolved in an inert organic solvent such as diethyl ether, ethyl acetate, chloroform, ethanol, methanol, and the like, and the acid is added in a similar solvent. The mixture is maintained at a suitable temperature (e.g., between 0° C. and 50° C.). The resulting salt precipitates spontaneously or can be brought out of solution with a less polar solvent.

The compounds of formula I of the present invention can exist in tautomeric forms, such as keto-enol tautomers. Such tautomeric forms are contemplated as an objective of this invention and such tautomers may be in equilibrium or predominant in one of the forms.

The prodrugs can be prepared in situ during the isolation and purification of the compounds, or by separately reacting the purified compound with a suitable derivatizing agent. For example, hydroxy groups can be converted into esters via treatment with a carboxylic acid in the presence of a catalyst. Examples of cleavable alcohol prodrug moieties include substituted or unsubstituted, branched or unbranched lower alkyl ester moieties, e.g., ethyl esters, lower alkenyl esters, di-lower alkylamino lower-alkyl esters, e.g., dimethylaminoethyl ester, acylamino lower alkyl esters, acyloxy lower alkyl esters (e.g., pivaloyloxymethyl ester), aryl esters, e.g., phenyl ester, aryl-lower alkyl esters, e.g., benzyl ester, substituted- or unsubstituted, e.g., with methyl, halo, or methoxy substituents aryl and aryl-lower alkyl esters, amides, lower-alkyl amides, di-lower alkyl amides, and hydroxy amides.

The term "prodrug" denotes a derivative of a compound, which derivative, when administered to warm-blooded animals, e.g. humans, is converted into the compound (drug).

The enzymatic and/or chemical hydrolytic cleavage of the compounds of the present invention occurs in such a manner that the proven drug form (parent carboxylic acid drug) is released, and the moiety or moieties split off remain nontoxic or are metabolized so that nontoxic metabolic products are produced. For example, a carboxylic acid group can be esterified, e.g., with a methyl group or ethyl group to yield an ester. When an ester is administered to a subject, the ester is cleaved, enzymatically or non-enzymatically, reductively, oxidatively, or hydrolytically, to reveal the anionic group. An anionic group can be esterified with moieties (e.g., acyloxymethyl esters) which are cleaved to reveal an intermediate compound which subsequently decomposes to yield the active compound.

The inhibitors mentioned in the present invention can be combined with antiinflammatory agents or agents that show therapeutic benefit for conditions including but not limited to hepatomegaly, heart failure, cardiomegaly, diabetes, stroke, alzheimer's disease, cystic fibrosis, septic shock or asthma, diabetic retinopathy, ischemic retinal vein occlusion, macular degeneration, neovascular glaucoma, psoriasis, inflammation, rheumatoid arthritis, restenosis, in-stent restenosis, and vascular graft restenosis.

The term "aberrant kinase activity" refers to any abnormal expression or activity of the gene encoding the kinase or of the polypeptide it encodes. Examples of such aberrant kinase activity include but are not limited to over-expression of the gene or polypeptide, gene amplification, mutations that produce constitutively active or hyperactive kinase activity, gene mutations, deletions, substitutions, additions, and the like.

Thus the present invention further provides a pharmaceutical composition, containing the compounds of the general formula (I) as defined above, its tautomeric forms, its pharmaceutically acceptable salts in combination with the usual pharmaceutically acceptable carriers, diluents, excipients and the like.

The pharmaceutically acceptable carrier (or excipient) is preferably one that is chemically inert to the compound of the invention and one that has no detrimental side effects or toxicity under the conditions of use. Such pharmaceutically acceptable carriers or excipients include saline (e.g., 0.9% saline), Cremophor EL (which is a derivative of castor oil and ethylene oxide available from Sigma Chemical Co., St. Louis, Mo.) (e.g., 5% Cremophor EL/5% ethanol/90% saline, 10% Cremophor EL/90% saline, or 50% Cremophor EL/50% ethanol), propylene glycol (e.g., 40% propylene glycol/10% ethanol/50% water), polyethylene glycol (e.g., 40% PEG 400/60% saline), and alcohol (e.g., 40% ethanol/60% water). A preferred pharmaceutical carrier is polyethylene glycol, such as PEG 400, and particularly a composition comprising 40% PEG 400 and 60% water or saline. The choice of carrier will be determined in part by the particular compound chosen, as well as by the particular method used to administer the composition. Accordingly, there is a wide variety of suitable formulations of the pharmaceutical composition of the present invention.

The following formulations for oral, aerosol, parenteral, subcutaneous, intravenous, intraarterial, intramuscular, interperitoneal, rectal, and vaginal administration are merely exemplary and are in no way limiting.

The pharmaceutical compositions can be administered parenterally, e.g., intravenously, intraarterially, subcutaneously, intradermally, intrathecally, or intramuscularly. Thus, the invention provides compositions for parenteral administration that comprise a solution of the compound of the invention dissolved or suspended in an acceptable carrier suitable for parenteral administration, including aqueous and non-aqueous, isotonic sterile injection solutions.

Overall, the requirements for effective pharmaceutical carriers for parenteral compositions are well known to those of ordinary skill in the art. See *Pharmaceutics and Pharmacy Practice*, J. B. Lippincott Company, Philadelphia, Pa., Banker and Chalmers, eds., pages 238-250 (1982), and *ASHP Handbook on Injectable Drugs*, Toissel, 4th ed., pages 622-630 (1986). Such compositions include solutions containing anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol (for example in topical applications), or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride, with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils useful in parenteral formulations include petroleum, animal, vegetable, and synthetic oils.

Specific examples of oils useful in such formulations include peanut, soybean, sesame, cottonseed, corn, olive, petrolatum, and mineral oil. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl-β-aminopropionates, and 2-alkyl-imidazoline quaternary ammonium salts, and (e) mixtures thereof.

The parenteral formulations typically will contain from about 0.5% or less to about 25% or more by weight of a compound of the invention in solution. Preservatives and buffers can be used. In order to minimize or eliminate irritation at the site of injection, such compositions can contain one or more nonionic surfactants having a hydrophile-lipophile balance (HLB) of from about 12 to about 17. The quantity of surfactant in such formulations will typically range from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

Topical formulations, including those that are useful for transdermal drug release, are well known to those of skill in the art and are suitable in the context of the present invention for application to skin.

Formulations suitable for oral administration can consist of (a) liquid solutions, such as an effective amount of a compound of the invention dissolved in diluents, such as water, saline, or orange juice; (b) capsules, sachets, tablets, lozenges, and troches, each containing a pre-determined amount of the compound of the invention, as solids or granules; (c) powders; (d) suspensions in an appropriate liquid; and (e) suitable emulsions. Liquid formulations can include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the compound ingredient in a flavor, usually sucrose and acacia or tragacanth, as well as pastilles comprising a compound of the invention in an inert base, such as gelatin and glycerin, or sucrose and acacia, emulsions, gels, and the like containing, in addition to the compound of the invention, such excipients as are known in the art.

A compound of the present invention, alone or in combination with other suitable components, can be made into aerosol formulations to be administered via inhalation. A compound or epimer of the invention is preferably supplied in finely divided form along with a surfactant and propellant. Typical percentages of the compounds of the invention can be about 0.01% to about 20% by weight, preferably about 1% to about 10% by weight. The surfactant must, of course, be nontoxic, and preferably soluble in the propellant. Representative of such surfactants are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides can be employed. The surfactant can constitute from about 0.1% to about 20% by weight of the composition, preferably from about 0.25% to about 5%. The balance of the composition is ordinarily propellant. A carrier can also be included as desired, e.g., lecithin, for intranasal delivery. These aerosol formulations can be placed into acceptable pressurized propellants, such as dichlorodifluoromethane, propane, nitrogen, and the like. They also can be formulated as pharmaceuticals for non-pressured preparations, such as in a nebulizer or an atomizer. Such spray formulations can be used to spray mucosa.

Additionally, the compound of the invention can be made into suppositories by mixing with a variety of bases, such as emulsifying bases or water-soluble bases. Formulations suitable for vaginal administration can be presented as pessaries, tampons, creams, gels, pastes, foams, or spray formulas containing, in addition to the compound ingredient, such carriers as are known in the art to be appropriate.

The concentration of the compound in the pharmaceutical formulations can vary, e.g., from less than about 1% to about 10%, to as much as 20% to 50% or more by weight, and can be selected primarily by fluid volumes, and viscosities, in accordance with the particular mode of administration selected.

For example, a typical pharmaceutical composition for intravenous infusion could be made up to contain 250 ml of sterile Ringer's solution, and 100 mg of at least one compound of the invention. Actual methods for preparing parenterally administrable compounds of the invention will be known or apparent to those skilled in the art and are described in more detail in, for example, *Remington's Pharmaceutical Science* (17$^{th}$ ed., Mack Publishing Company, Easton, Pa., 1985).

It will be appreciated by one of ordinary skill in the art that, in addition to the aforedescribed pharmaceutical compositions, the compound of the invention can be formulated as inclusion complexes, such as cyclodextrin inclusion complexes, or liposomes. Liposomes can serve to target a compound of the invention to a particular tissue, such as lymphoid tissue or cancerous hepatic cells. Liposomes can also be used to increase the half-life of a compound of the invention. Many methods are available for preparing liposomes, as described in, for example, Szoka et al., *Ann. Rev. Biophys. Bioeng.*, 9, 467 (1980) and U.S. Pat. Nos. 4,235,871, 4,501,728, 4,837,028, and 5,019,369.

The compounds of the invention can be administered in a dose sufficient to treat the disease, condition or disorder. Such doses are known in the art (see, for example, the *Physicians' Desk Reference* (2004)). The compounds can be administered using techniques such as those described in, for example, Wasserman et al., *Cancer*, 36, pp. 1258-1268 (1975) and *Physicians' Desk Reference*, 58th ed., Thomson PDR (2004).

Suitable doses and dosage regimens can be determined by conventional range-finding techniques known to those of ordinary skill in the art. Generally, treatment is initiated with smaller dosages that are less than the optimum dose of the compound of the present invention. Thereafter, the dosage is increased by small increments until the optimum effect under the circumstances is reached. The present method can involve the administration of about 0.1 µg to about 50 mg of at least one compound of the invention per kg body weight of the individual. For a 70 kg patient, dosages of from about 10 µg to about 200 mg of the compound of the invention would be more commonly used, depending on a patient's physiological response.

By way of example and not intending to limit the invention, the dose of the pharmaceutically active agent(s) described herein for methods of treating or preventing a disease or condition as described above can be about 0.001 to about 1 mg/kg body weight of the subject per day, for example, about 0.001 mg, 0.002 mg, 0.005 mg, 0.010 mg, 0.015 mg, 0.020 mg, 0.025 mg, 0.050 mg, 0.075 mg, 0.1 mg, 0.15 mg, 0.2 mg, 0.25 mg, 0.5 mg, 0.75 mg, or 1 mg/kg body weight per day. The dose of the pharmaceutically active agent(s) described herein for the described methods can be about 1 to about 1000 mg/kg body weight of the subject being treated per day, for example, about 1 mg, 2 mg, 5 mg, 10 mg, 15 mg, 0.020 mg, 25 mg, 50 mg, 75 mg, 100 mg, 150 mg, 200 mg, 250 mg, 500 mg, 750 mg, or 1000 mg/kg body weight per day.

The terms "treat," "prevent," "ameliorate," and "inhibit," as well as words stemming therefrom, as used herein, do not necessarily imply 100% or complete treatment, prevention, amelioration, or inhibition. Rather, there are varying degrees of treatment, prevention, amelioration, and inhibition of which one of ordinary skill in the art recognizes as having a potential benefit or therapeutic effect. In this respect, the disclosed methods can provide any amount of any level of treatment, prevention, amelioration, or inhibition of the disorder in a mammal. For example, a disorder, including symptoms or conditions thereof, may be reduced by, for example, 100%, 90%, 80%, 70%, 60%, 50%, 40%, 30%, 20%, or 10%. Furthermore, the treatment, prevention, amelioration, or inhibition provided by the inventive method can include treatment, prevention, amelioration, or inhibition of one or more conditions or symptoms of the disorder, e.g., cancer. Also, for purposes herein, "treatment," "prevention," "amelioration," or "inhibition" can encompass delaying the onset of the disorder, or a symptom or condition thereof.

In accordance with the invention, the term subject includes an "animal" which in turn includes a mammal such as, without limitation, the order Rodentia, such as mice, and the order Lagomorpha, such as rabbits. In one aspect that the mammals are from the order Carnivora, including Felines (cats) and Canines (dogs). In another aspect the mammals are from the order Artiodactyla, including Bovines (cows) and Swine (pigs) or of the order Perssodactyla, including Equines (horses). In a further aspect, the mammals are of the order Primates, Ceboids, or Simoids (monkeys) or of the order Anthropoids (humans and apes). In yet another aspect, the mammal is the human.

General Method of Preparation

The compounds of general formula (I) where all the symbols are as defined earlier can be prepared by methods given in below schemes or examples illustrated herein below.

However, the disclosure should not be construed to limit the scope of the invention arriving at compound of formula (I) disclosed hereinabove.

Scheme 1 ($R^1$ is H)

Compound of formula (I) where $R^1$ is H, can be prepared as depicted in Scheme 1, details of which are given below.

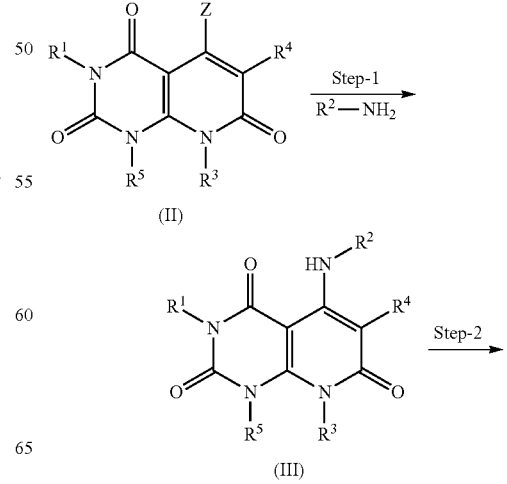

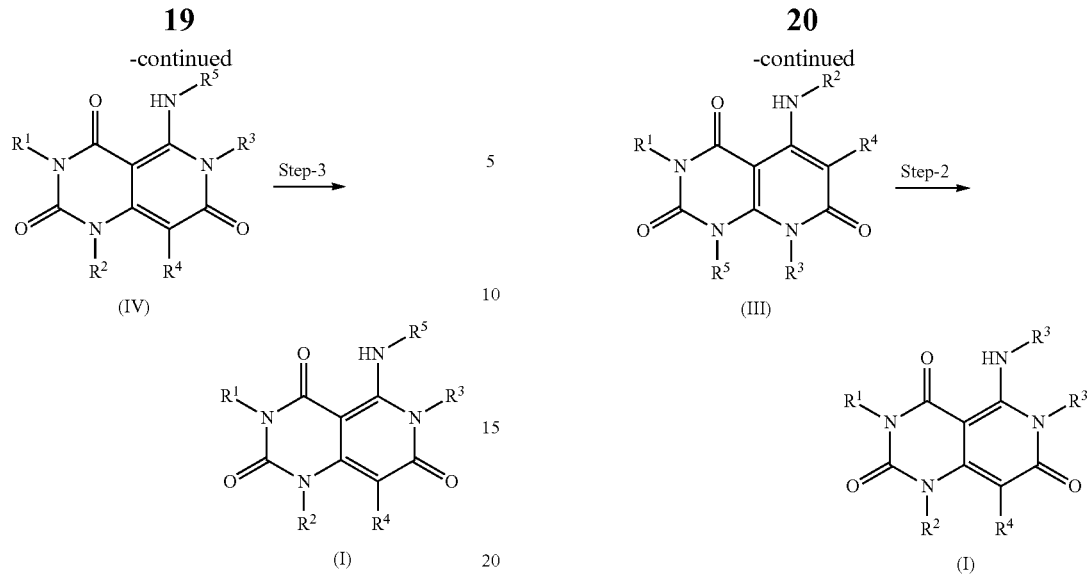

(IV)

(I)

(III)

(I)

Step-1

Compound of formula (II) where $R^1$ is N-protecting group, can be converted to compound of formula (III) by reacting compound of II (Z is any suitable leaving group like Cl, Br, I, —O(SO)$_2$(4-MePh), —O(SO)$_2$CH$_3$, —O(SO)$_2$CF$_3$ etc.) with $R^2NH_2$ in presence of a suitable base like 2,6-Lutidine, 1,8-Diazabicyclo[5.4.0]undec-7-ene (DBU), K$_2$CO$_3$, Cs$_2$CO$_3$, NaH, KH, n-BuLi, lithium bis(trimethylsilyl)amide (LiHMDS) etc., in a solvent like THF, DMF, DMSO etc., at temperature ranging from about −78° C. to about 150° C.

Step-2

Compound of formula-(III) where $R^1$ is N-protecting group, can be converted to compound of formula-(IV) by reacting compound of formula (III) with suitable base such as NaOMe, K$_2$CO$_3$ etc. in a solvent like Methanol, Ethanol, THF, DMF etc. at temperature ranging from about −78° C. to about 150° C.

Step-3

Compound of formula-(IV) where $R^1$ is N-protecting group, can be converted to compound of formula-(I) by reacting compound of formula (IV) with suitable N-deprotection agents such as AlCl$_3$, Pd—C/H$_2$ etc. in a solvent like Anisole, Toluene, Xylene, THF, DMF, DMSO etc. at temperature ranging from about −78° C. to about 150° C.

Scheme-2

Compound of formula (I) where $R^1$ is selected from the group consisting of substituted- or unsubstituted-alkyl, substituted- or unsubstituted-alkenyl, substituted- or unsubstituted-alkynyl, substituted- or unsubstituted-cycloalkyl, substituted- or unsubstituted-cycloalkenyl, substituted- or unsubstituted-aryl, substituted- or unsubstituted-heteroaryl, and substituted- or unsubstituted-heterocyclyl, can be prepared as depicted in Scheme 2, details of which are given below Scheme 2

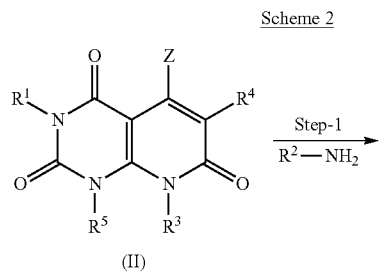

(II)

Step-1

Compound of formula (II) where $R^1$ is selected from substituted- or unsubstituted-alkyl, substituted- or unsubstituted-alkenyl, substituted- or unsubstituted-alkynyl, substituted- or unsubstituted-cycloalkyl, substituted- or unsubstituted-cycloalkenyl, substituted- or unsubstituted-aryl, substituted- or unsubstituted-heteroaryl, and substituted- or unsubstituted-heterocyclyl, can be converted to compound of formula (III) by reacting compound of II (Z is any suitable leaving group like Cl, Br, I, —O(SO)$_2$(4-MePh), —O(SO)$_2$CH$_3$, —O(SO)$_2$CF$_3$ etc.) with $R^2NH_2$ in presence of a suitable base like 2,6-Lutidine, 1,8-Diazabicyclo[5.4.0] undec-7-ene (DBU), K$_2$CO$_3$, Cs$_2$CO$_3$, NaH, KH, n-BuLi, lithium bis(trimethylsilyl)amide (LiHMDS) etc., in a solvent like THF, DMF, DMSO etc., at temperature ranging from about −78° C. to about 150° C.

Step-2

Compound of formula-(III) where $R^1$ is selected from substituted- or unsubstituted-alkyl, substituted- or unsubstituted-alkenyl, substituted- or unsubstituted-alkynyl, substituted- or unsubstituted-cycloalkyl, substituted- or unsubstituted-cycloalkenyl, substituted- or unsubstituted-aryl, substituted- or unsubstituted-heteroaryl, and substituted- or unsubstituted-heterocyclyl, can be converted to compound of formula-(I) by reacting compound of formula (III) with suitable base such as NaOMe, K$_2$CO$_3$ etc. in a solvent like Methanol, Ethanol, THF, DMF etc. at temperature ranging from about −78° C. to about 150° C.

The intermediates and the compounds of the present invention are obtained in pure form in a manner known per se, for example by distilling off the solvent in vacuum and re-crystallizing the residue obtained from a suitable solvent, such as pentane, diethyl ether, isopropyl ether, chloroform, dichloromethane, ethyl acetate, acetone or their combinations or subjecting it to one of the purification methods, such as column chromatography (e.g. flash chromatography) on a suitable support material such as alumina or silica gel using eluent such as dichloromethane, ethyl acetate, hexane, methanol, acetone and their combinations. Preparative LC-MS method is also used for the purification of molecules described herein.

Salts of compound of formula I are obtained by dissolving the compound in a suitable solvent, for example in a chlorinated hydrocarbon, such as methyl chloride or chloroform or a low molecular weight aliphatic alcohol, for example, ethanol or isopropanol, which was then treated with the desired acid or base as described in Berge S. M. et al. "Pharmaceutical Salts, a review article in Journal of Pharmaceutical sciences volume 66, page 1-19 (1977)" and in handbook of pharmaceutical salts properties, selection, and use by P. H. Einrich Stahland Camille G. wermuth, Wiley-VCH (2002).

EXAMPLES

The following examples are provided to further illustrate the present invention and therefore should not be construed in any way to limit the scope of the present invention. All $^1$HNMR spectra were determined in the solvents indicated and chemical shifts are reported in δ units downfield from the internal standard tetramethylsilane (TMS) and interproton coupling constants are reported in Hertz (Hz).

Unless otherwise stated, work-up includes distribution of the reaction mixture between the organic and aqueous phase indicated within parentheses, separation of layers and drying the organic layer over sodium sulphate, filtration and evaporation of the solvent. Purification, unless otherwise mentioned, includes purification by silica gel chromatographic techniques, generally using a mobile phase with suitable polarity. The following abbreviations are used in the text: DMSO-d6: Hexadeuterodimethyl sulfoxide; DMSO: Dimethylsulfoxide, DMF: N,N-dimethyl formamide, DMA: Dimethylacetamide, THF: Tetrahydrofuran, TFA: Trifluoroacetic acid, DAST: Diethylarninosulfur trifluoride; DCM: Dichloromethane, m-CPBA: meta-Chloroperoxybenzoic acid, EDC: 1-Ethyl-3-(3-dimethylaminopropyl)carbodiimide, J: Coupling constant in units of Hz, RT or rt: room temperature (22-26° C.), Aq.: aqueous, AcOEt: ethyl acetate, equiv. or eq.: equivalents and hr. or h: hour(s)

Intermediates

Intermediate-i: Synthesis of
3-(cyclopropylsulfonyl)aniline

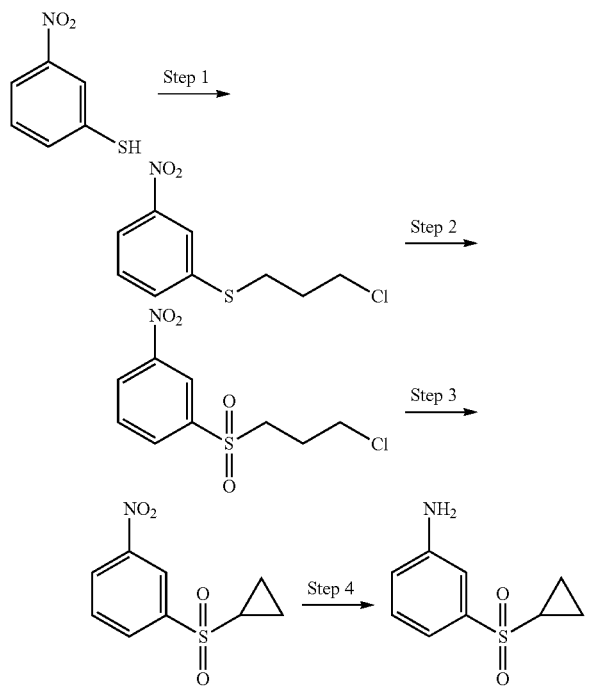

Step 1: Synthesis of
3-chloropropyl)(3-nitrophenyl)sulfane

To a suspension of 3-nitrobenzenethiol (2.3 g, 14.82 mmol) and NaOH (1.186 g, 29.6 mmol) in Ethanol (40.0 ml) was added 1-bromo-3-chloropropane (1.75 ml, 17.79 mmol). The resulting mixture was stirred at RT under inert atmosphere for 18 h. Solvent was evaporated under vacuum and the residue was partitioned between DCM (200 ml) and water (100 ml). The organic layer was separated and washed with brine (100 ml), dried over anhydrous sodium sulphate and evaporated under vacuum. The residual oil was purified by column chromatography over silicagel, using 15% EtOAc in Hexane as eluent to afford (3-chloropropyl)(3-nitrophenyl)sulfane (2.92 g, 12.60 mmol, 85% yield).

$^1$H NMR (400 MHz, CDCl$_3$) δ 8.14-8.16 (m, 1H), 8.05-8.00 (m, 1H), 7.65-7.60 (m, 1H), 7.49-7.43 (m, 1H), 3.70 (t, J=6.2 Hz, 2H), 3.2 (t, J=7.2 Hz, 2H), 2.18-2.12 (m, 2H). GCMS: 231.04 [M+]

Step 2: Synthesis of
1-((3-chloropropyl)sulfonyl)-3-nitrobenzene m-CPBA (7.45 g, 32.4 mmol) was added to a solution of (3-chloropropyl)(3-nitrophenyl)sulfane (3 g, 12.95 mmol) in CHCl$_3$ (50 mL). Resulting mixture was stirred at RT for 18 hrs and filtered to remove most of the benzoic acid. The filtrate was diluted with CHCl$_3$ (100 ml) and washed with 10% aq. NaOH (100 ml). Organic phase was dried over anhydrous sodium sulphate and evaporated under vacuum. Residue was purified by silicagel column chromatography eluting with 30% EtOAc:Hexane to afford 1-((3-chloropropyl)sulfonyl)-3-nitrobenzene (2.75 g).

$^1$H NMR (400 MHz, CDCl$_3$) δ 8.79 (brs, 1H), 8.55 (d, J=8.0 Hz, 1H), 8.28 (d, J=7.6 Hz, 1H), 7.88-7.84 (m, 1H), 3.68 (t, J=6.0 Hz, 2H), 3.37 (t, J=7.6 Hz, 2H), 2.32-2.25 (m, 2H). GCMS: 262.96 [M+]

Step 3: Synthesis of
1-(cyclopropylsulfonyl)-3-nitrobenzene

Potassium tert-butoxide (2.13 g, 18.96 mmol) was added to a solution of 1-((3-chloropropyl)sulfonyl)-3-nitrobenzene (2 g, 7.58 mmol) in t-BuOH (10 ml) at RT. Resulting solution was stirred at RT for 5 h. Solvent was evaporated under vacuum. Residue was partitioned between EtOAc (150 ml) and water (150 ml). Organic phase was removed and dried over sodium sulphate. Solvent was evaporated under vacuum to obtain 1-(cyclopropylsulfonyl)-3-nitrobenzene (1.206 g, 5.31 mmol, 70% yield), which was carried forward to the next step without further purification.

$^1$H NMR (400 MHz, CDCl$_3$) δ 8.78 (brs, 1H), 8.52 (d, J=8.0 Hz, 1H), 8.26 (d, J=7.6 Hz, 1H), 7.84-7.80 (m, 1H), 2.55-2.52 (m, 1H), 1.45-1.38 (m, 2H), 1.15-1.13 (m, 2H). GCMS: 227.01 [M+]

Step 4: Synthesis of 3-(cyclopropylsulfonyl)aniline

Triethylsilane (14 ml, 88 mmol) was added dropwise to a suspension of 1-(cyclopropylsulfonyl)-3-nitrobenzene (2 g, 8.80 mmol) and Pd/C (10%, 250 mg) in MeOH (25 ml). Resulting suspension was stirred at RT for 20 min. and filtered through celite. The filtrate was evaporated under vacuum and triturated in hexane to obtain the crystals which were collected by filtration to afford 3-(cyclopropylsulfonyl) aniline (1.44 gm).

$^1$H NMR (400 MHz, DMSO-d$_6$) δ 7.24 (t, J=8.0 Hz, 1H), 7.03-7.02 (m, 1H), 6.95-6.92 (m, 1H), 6.84-6.81 (m, 1H), 5.66 (s, 2H), 2.74-2.70 (m, 1H), 1.05-0.95 (m, 4H). GCMS: 197.03 [M+].

Intermediate-ii: Synthesis of N-(3-aminophenyl)-3-methyloxetane-3-carboxamide

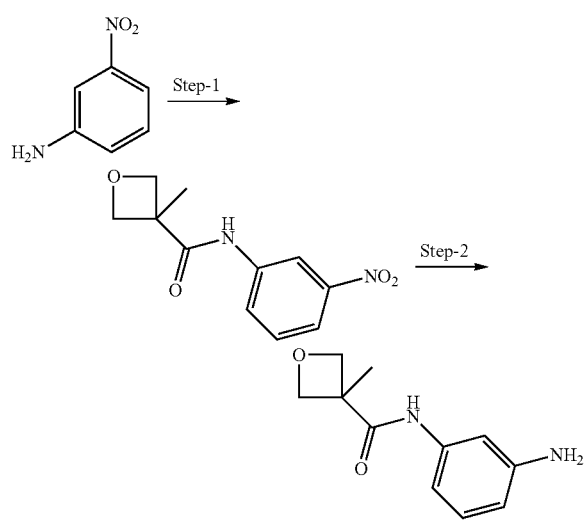

Step-1: Synthesis of 3-methyl-N-(3-nitrophenyl) oxetane-3-carboxamide

To a stirred solution of 3-nitroaniline (0.297 g, 2.153 mmol) in pyridine (1 ml), was added 3-methyloxetane-3-carboxylic acid (0.250 g, 2.153 mmol) and EDC.HCl (0.619 g, 3.23 mmol). The reaction mixture was stirred at room temperature for 2 hrs. and then concentrated under vacuum, the residue was diluted with water (10 ml) and extracted with ethyl acetate (3×7 ml). The combined organic layer was washed with brine and water, dried over sodium sulfate and concentrated under vacuum to afford the title compound (400 mg).

$^1$HNMR (400 MHz, CDCl$_3$): δ 8.45 (t, 1H, J=2 Hz), 8.06 (bs, 1H), 8.02-7.99 (m, 2H), 7.54 (t, 1H, J=4 Hz), 4.95 (d, 2H, J=6.4 Hz), 4.65 (d, 2H, J=6.4 Hz), 1.68 (s, 3H). GCMS: 236 (M+)

Step-2: Synthesis of N-(3-aminophenyl)-3-methyloxetane-3-carboxamide

To a stirred solution of 3-methyl-N-(3-nitrophenyl) oxetane-3-carboxamide (0.5 g, 2.117 mmol) in Ethyl acetate (5 ml), 10% Pd/C (0.225 g) was added and the reaction mixture was stirred room temperature for 10 hrs under hydrogen atmosphere. The reaction mixture was filtered through celite and concentrated under vacuum to afford the title product (0.400 g).

GCMS: 206 (M+).

Intermediate-iii: Synthesis of 3-(3-aminophenyl) oxetan-3-ol

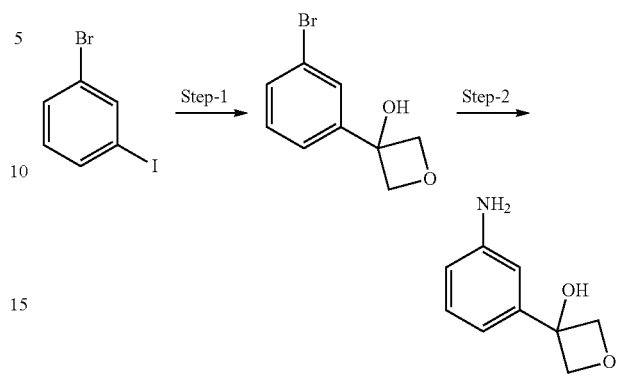

Step-1: Synthesis of 3-(3-bromophenyl) oxetan-3-ol

To a stirred solution of 1-bromo-3-iodobenzene (0.500 g, 1.767 mmol) in THF (5 ml), at 78° C. was added n-butyl-lithium (1.1 ml, 1.767 mmol). The reaction mixture was stirred at same temperature for 1 hr, then oxetan-3-one (0.127 g, 1.767 mmol) was added. The reaction mixture was stirred at −40° C. for one hour and saturated ammonium chloride solution was added. The reaction mixture was extracted with ethyl acetate (3×5 ml). Combined organic layer was dried over sodium sulfate and concentrated under vacuum to afford the crude product which was purified by column chromatography over silica gel using 30% ethyl acetate in hexane as eluent to give the title product (80 mg).

$^1$HNMR (400 MHz, CDCl$_3$): δ 7.80 (t, 1H, J=2 Hz), 7.51-7.48 (m, 1H), 7.32 (t, 1H, J=7.6 Hz), 5.60-5.57 (m, 1H), 4.93-4.87 (m, 4H), 2.52 (s, 1H).

Step-2: Synthesis of 3-(3-aminophenyl) oxetan-3-ol

To a stirred mixture of 3-(3-bromophenyl)oxetan-3-ol (0.2 g, 0.873 mmol) in aq. ammonia (1 ml), copper(II) oxide (0.069 g, 0.873 mmol) was added and the mixture was heated at 90° C. for 24 hrs in a sealed tube. The reaction mixture was cooled to room temperature and ethyl acetate (10 ml) was added, the reaction mixture was filtered through celite and the filtrate was concentrated under vacuum to afford title product (0.1 g).

$^1$HNMR (400 MHz, CDCl$_3$): δ 7.21 (t, 1H, J=7.6 Hz), 7.0-6.97 (m, 1H), 6.93-6.92 (m, 1H), 6.67-6.65 (m, 1H), 4.90 (s, 4H), 3.79 (bs, 2H), 3.02 (bs, 1H). GCMS: 165 (M+).

Intermediate-iv: Synthesis of 3-(azetidin-1-yl) aniline

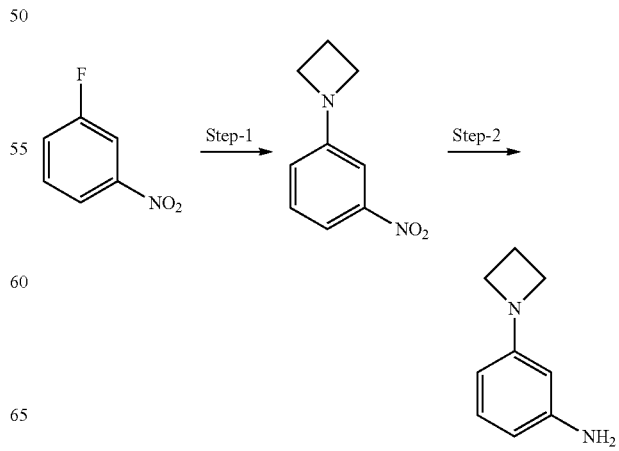

Step-1: Synthesis of 1-(3-nitrophenyl) azetidine

A stirred mixture of 1-fluoro-3-nitrobenzene (0.305 g, 2.161 mmol), Azetidine.HCl (0.2 g, 2.161 mmol) and $K_2CO_3$ (0.747 g, 5.40 mmol) in DMSO (5 ml) was heated at 86° C. for 24 hrs. The reaction mixture was cooled to room temperature and water was added (25 ml), the mixture was extracted with ethyl acetate (3×10 ml). Combined organic layer was dried over sodium sulfate and concentrated under vacuum to afford the crude compound, which was then purified by column chromatography (40 mg).

$^1$HNMR (400 MHz, $CDCl_3$): 7.55-7.52 (m, 1H), 7.31 (t, 1H, J=8 Hz), 7.20 (t, 1H, J=2.4 Hz), 6.70-6.67 (m, 1H), 3.97 (t, 4H, J=7.6 Hz), 2.48-2.41 (m, 2H). GCMS: 178 (M+).

Step-2: Synthesis of 3-(azetidin-1-yl) aniline

To a stirred solution of 1-(3-nitrophenyl)azetidine (0.040 g, 0.224 mmol) in Ethyl acetate (2 ml) was added Pd/C (10%, 0.01 mg) and the reaction mixture was heated at 55° C. for 12 hrs under hydrogen atmosphere. The reaction mixture was cooled to room temperature and diluted with ethyl acetate (10 ml) and the mixture was filtered through celite, and the filtrate was concentrated under vacuum to afford the title compound (30 mg, 90%).

$^1$HNMR (400 MHz, $CDCl_3$): 7.02 (t, 1H, J=8 Hz), 6.12-6.10 (m, 1H), 5.93-5.90 (m, 1H), 5.80-5.79 (m, 1H), 3.85 (t, 4H, J=7.2 Hz), 3.59 (bs, 2H), 2.37-2.30 (m, 2H). GCMS: 148 (M+)

Intermediate-v: Synthesis of tert-butyl 3-((3-aminophenyl)carbamoyl)azetidine-1-carboxylate

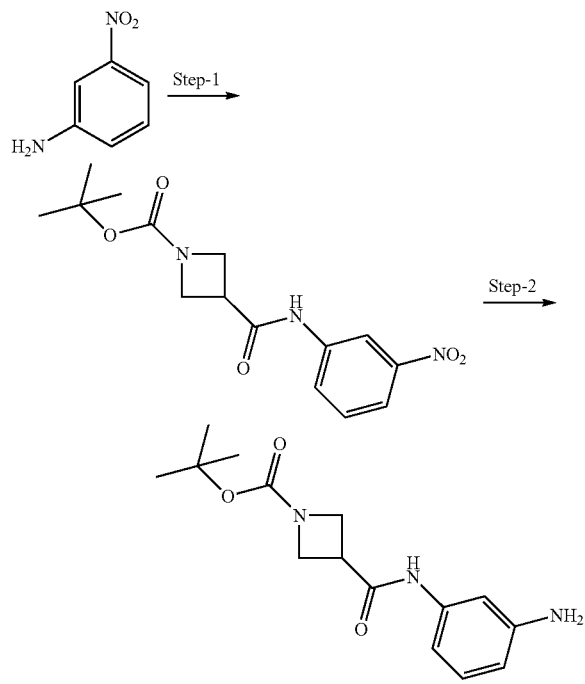

Step-1: Synthesis of tert-butyl 3-((3-nitrophenyl)carbamoyl)azetidine-1-carboxylate To 3-nitroaniline (0.137 g, 0.994 mmol) in pyridine (6 ml) were added 1-(tert-butoxycarbonyl)azetidine-3-carboxylic acid (0.5 g, 2.485 mmol) and EDC. HCl (0.715 g, 3.73 mmol). After being stirred at room temperature for 2 hrs reaction mixture was concentrated under vacuum. Diluted above reaction mixture with water (10 ml) extracted with 3×7 ml chloroform: IPA (3:1). Washed organic layer with brine and water, dried over sodium sulfate and concentrated to afford titled compound (300 mg, 38%).

ESI-MS m/z: 322 (M+1).

Step-2: Synthesis of tert-butyl 3-((3-aminophenyl)carbamoyl)azetidine-1-carboxylate To a stirred solution of tert-butyl 3-((3-nitrophenyl)carbamoyl)azetidine-1-carboxylate (0.3 g, 0.934 mmol) in methanol (10 ml) was added ammonium formate (0.3 g, 4.76 mmol) and Pd/C (10%, 0.05 g) and the mixture was stirred at room temperature for 10 hrs., since reaction was not complete so, Pd/C (0.05 g) and ammonium formate (0.3 g, 4.76 mmol) were added again and the stirring was continued for further 6 hrs. The reaction mixture was filtered through celite and the filtrate was concentrated. The residue was purified by column chromatography over silica gel using ethyl acetate in hexane as eluent to afford the title compound (200 mg).

ESI-MS m/z: 292 (M+1)

Intermediate-vi: Synthesis of 1-(3-aminophenyl)azetidin-3-ol

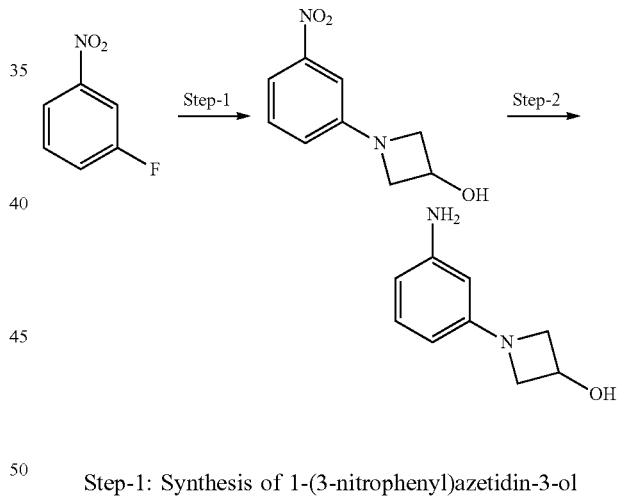

Step-1: Synthesis of 1-(3-nitrophenyl)azetidin-3-ol

Azetidin-3-ol hydrochloride (1.0 g, 9.13 mmol) was taken in DMSO and 1-fluoro-3-nitrobenzene (1.0 g, 7.09 mmol) was added followed by $K_2CO_3$ (2.449 g, 17.72 mmol). The reaction mixture was heated to 100° C. for 16 hrs. After completion of the reaction, the reaction mixture was cooled and poured into water which was then extracted with ethyl acetate (3×8 ml). The organic layers were combined, washed with water and brine, dried over sodium sulfate, and concentrated under vacuum. The resulting crude product was purified by column chromatography to yield the titled compound 1-(3-nitrophenyl)azetidin-3-ol (0.73 g).

$^1$H NMR (400 MHz, $CDCl_3$) δ 7.58 (dd, 1H, J=1.6 and 8 Hz), 7.33 (t, 1H, 8 Hz), 7.24 (t, 1H, J=2 Hz), 6.73-6.71 (m, 1H), 4.86-4.84 (m, 1H), 4.28-4.26 (m, 2H), 3.80-3.77 (m, 2H), 2.18 (d, 1H, J=6.4 Hz). ESI-MS [m/z=194 [M+1]].

Step-2: Synthesis of 1-(3-aminophenyl)azetidin-3-ol

In ethyl acetate (10 ml), 1-(3-nitrophenyl)azetidin-3-ol (0.43 g, 2.214 mmol) was taken and Pd/C (10%, 0.04 g) was added and the reaction mixture was stirred under hydrogen atmosphere at room temperature for 10 hrs. After completion of the reaction, the reaction mixture was filtered through celite, residue was washed with ethyl acetate (3×5 ml). Combined filtrate was concentrated under vacuum to yield the title compound (0.35 g).

$^1$H NMR (400 MHz, CDCl$_3$) δ 7.01 (t, 1H, J=8 Hz), 6.15-6.12 (m, 1H), 5.95-5.92 (m, 1H), 5.81 (t, 1H, J=2.4 Hz), 4.73-4.69 (m, 1H), 4.16-4.12 (m, 2H), 3.66-3.62 (m, 4H), 1.73 (brs, 1H). ESI-MS [m/z=164 [M+1]].

Intermediate-vii: Synthesis of 1-(3-aminophenyl)azetidin-2-one

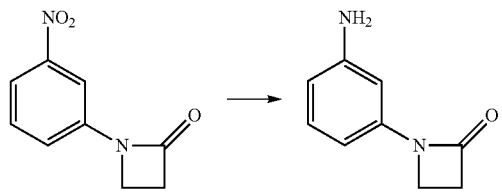 [SMILES: O=C1CCN1c1cccc([N+](=O)[O-])c1 ; Nc1cccc(N2CCC2=O)c1]

To a mixture of 1-(3-nitrophenyl)azetidin-2-one (600 mg, 3.12 mmol), ammonium formate (591 mg, 9.37 mmol) and methanol (40 ml) at 0° C., was added Pd/C (10%, 0.17 g) and the reaction mixture was stirred at 50° C. for 3 hrs. The reaction mixture was cooled to room temperature and filtered through celite, the filtrate was concentrated under vacuum. The residue was taken in ethyl acetate and filtered through celite and concentrated under vacuum to afford the yellow solid product (230 mg).

$^1$HNMR (400 MHz, CDCl$_3$): δ 7.11 (t, 1H, J=8 Hz), 6.92-6.91 (m, 1H), 6.59-6.57 (m, 1H), 6.44-6.41 (m, 1H), 3.75 (bs, 2H), 3.60 (t, 2H, J=4.4 Hz), 3.09 (t, 2H, J=4.4 Hz).

Intermediate-viii: Synthesis of 3-(oxetan-3-yloxy)aniline

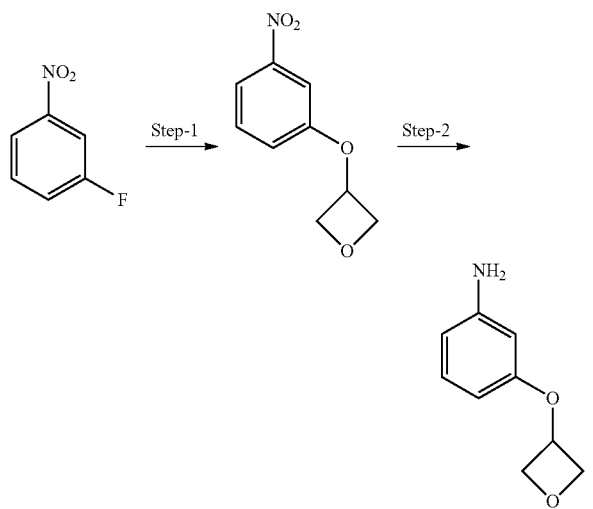 [SMILES: O=[N+]([O-])c1cccc(F)c1 ; O=[N+]([O-])c1cccc(OC2COC2)c1 ; Nc1cccc(OC2COC2)c1]

Step-1: Synthesis of 3-(3-nitrophenoxy)oxetane

Oxetan-3-ol (578 mg, 7.80 mmol) was taken in THF (8 ml) under nitrogen atmosphere, cooled to 0° C., KOtBu (962 mg, 8.58 mmol) was added and the mixture was stirred at same temperature for 30 min., 1-fluoro-3-nitrobenzene (0.41 ml, 3.90 mmol) was added and the reaction mixture was stirred at room temperature for 18 hrs. The reaction mixture was concentrated under vacuum and water (50 ml) was added, the mixture was extracted with ethyl acetate (3×20 ml). Combined organic layer was dried over sodium sulfate and the mixture was concentrated under vacuum to afford the crude product, which was purified by column chromatography to afford yellow solid product (350 mg).

GCMS: 195 (M+)

Step-2: Synthesis of 3-(oxetan-3-yloxy)aniline

To a mixture of 3-(3-Nitrophenoxy)oxetane (0.350 g, 1.793 mmol), ammonium formate (339 mg, 5.38 mmol) and methanol (40 ml) at 0° C., was added Pd/C (10%, 0.17 g) and the reaction mixture was stirred at 50° C. for 3 hrs. The reaction mixture was cooled to room temperature and filtered through celite, the filtrate was concentrated under vacuum. The residue was taken in ethyl acetate and filtered through celite and concentrated under vacuum to afford the yellow solid product (260 mg).

Intermediate-ix: Synthesis of 2-((1-(3-aminophenyl)azetidin-3-yl)oxy)acetamide

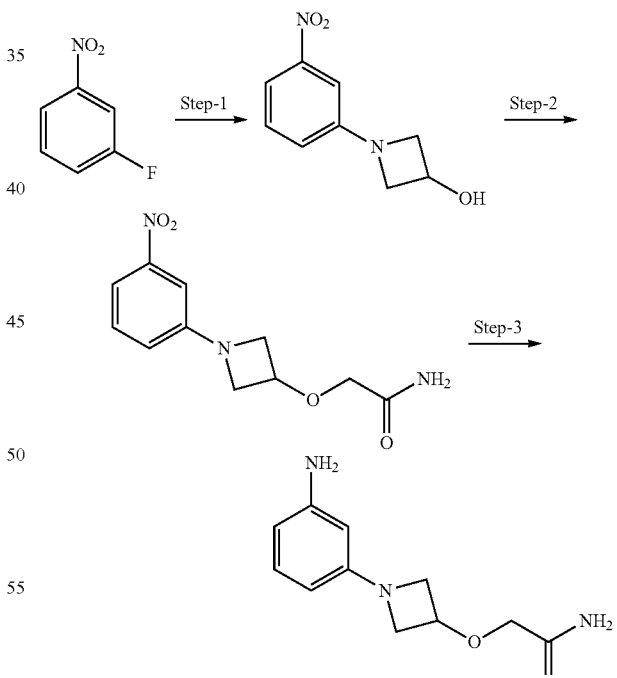

Step-1: Synthesis of 1-(3-nitrophenyl)azetidin-3-ol

Azetidin-3-ol hydrochloride (1.863 g, 17.01 mmol), 1-fluoro-3-nitrobenzene (2. g, 14.17 mmol) were taken in DMSO (20 ml) and K$_2$CO$_3$ (4.90 g, 35.4 mmol) was added to the mixture and the reaction mixture was heated at 110°

C. for 24 hrs. The reaction mixture was cooled to room temperature, water was added and the mixture was extracted with ethyl acetate (3×75 ml). Combined organic layer was dried over sodium sulphate and concentrated under vacuum to afford the crude product which was purified by column chromatography eluting with 0-20% ethyl acetate in hexane to afford the title product (1.1 g).

Step-2: Synthesis of 2-((1-(3-nitrophenyl)azetidin-3-yl)oxy)acetamide 1-(3-Nitrophenyl)azetidin-3-ol (1.2 g, 6.18 mmol), 2-bromoacetamide (1.023 g, 7.42 mmol) were taken in DMF (20 ml) and 60% NaH (0.741 g, 18.5 mmol) was added the to the mixture and the mixture was heated at 40° C. for 16 hrs. The reaction mixture was cooled to room temperature, water was added and the mixture was extracted with ethyl acetate (3×75 ml). Combined organic layer was dried over sodium sulphate and concentrated under vacuum to afford the crude product which was purified by column chromatography eluting with 0-20% ethyl acetate in hexane to afford the title product (0.8 g).

Step-3: Synthesis of 2-((1-(3-aminophenyl)azetidin-3-yl)oxy)acetamide 2-((1-(3-Nitrophenyl)azetidin-3-yl)oxy)acetamide (0.8 g, 3.18 mmol) was taken in methanol (20 ml) and at 0° C., Pd—C(10%, 0.07 g) was added. The reaction mixture was stirred under hydrogen atmosphere at room temperature for 5 hrs. The reaction mixture was filtered through celite and the filtrate was concentrated under vacuum to afford the title product (0.42 gm).

Intermediate-x: Synthesis of N1-(oxetan-3-yl)benzene-1,3-diamine

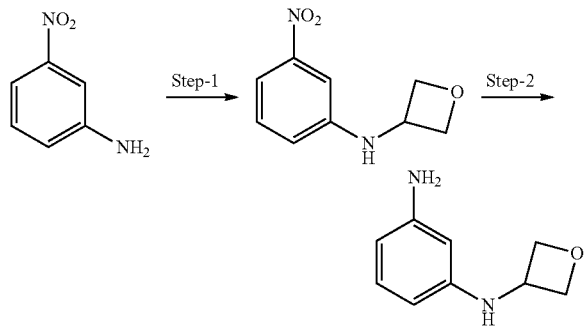

Step-1: Synthesis of N-(3-nitrophenyl)oxetan-3-amine

To a solution of 3-nitroaniline (2 g, 14.48 mmol) in methanol (30 ml), were added oxetan-3-one (1.565 g, 21.72 mmol) and zinc chloride (7.89 g, 57.9 mmol) and the reaction mixture was cooled with an ice bath. Sodium cyanoborohydride (2.73 g, 43.4 mmol) was added to the reaction mixture and the mixture was stirred at room temperature for 5 hrs. The reaction mixture was poured over cold aq. satd. ammonium chloride solution and extracted with ethyl acetate (3×75 ml). Combined organic layer was dried over sodium sulfate and concentrated under vacuum. The crude residue was adsorbed purified by column chromatography using 0-50% ethyl acetate in hexanes as eluent to afford the title product (1.2 g).

Step-2: Synthesis of N1-(oxetan-3-yl)benzene-1,3-diamine

N-(3-Nitrophenyl)oxetan-3-amine (0.55 g, 2.83 mmol) was taken in methanol (10 ml) and at 0° C., Pd—C(10%, 0.1 g) was added. The reaction mixture was stirred under hydrogen atmosphere at room temperature for 5 hrs. The reaction mixture was filtered through celite and the filtrate was concentrated under vacuum to afford the title product (0.4 gm).

¹HNMR (400 MHz, CDCl₃): δ 6.98 (t, 1H, J=8 Hz), 6.16-6.13 (m, 1H), 5.98-5.95 (m, 1H), 5.84 (t, 1H, J=2.4 Hz), 4.99 (t, 2H, J=6.4 Hz), 4.65-4.57 (m, 1H), 5.27 (t, 2H, J=6 Hz), 4.05 (d, 1H, J=6.4 Hz), 3.50 (bs, 2H).

Intermediate-xi: Synthesis of 3-((oxetan-3-yloxy)methyl)aniline

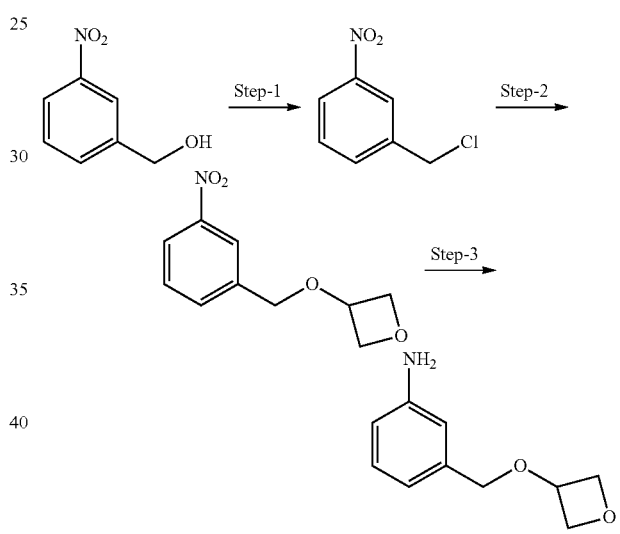

Step-1: Synthesis of 1-(chloromethyl)-3-nitrobenzene (3-Nitrophenyl)methanol (1 g, 6.53 mmol) was dissolved in DCM (8 ml) and cooled to 0° C. followed by addition of thionyl chloride (2.15 ml, 19.59 mmol). The Reaction mixture was stirred for 4 hrs at room temperature and concentrated under vacuum, saturated solution of sodium bicarbonate was added to the residue. The mixture was extracted with ethyl acetate (3×75 ml), combined organic layer was dried over sodium sulfate and concentrated under vacuum to afford the title compound (0.9 gm).

Step-2: Synthesis of 3-((3-nitrobenzyl)oxy)oxetane

A mixture of oxetan-3-ol (0.432 g, 5.83 mmol), K₂CO₃ (1.611 g, 11.66 mmol) and 1-(chloromethyl)-3-nitrobenzene (1 g, 5.83 mmol) in DMF (10 ml) was heated at 80° C. for 18 hrs. The reaction mixture was cooled to room temperature, water was added and the mixture was extracted with ethyl acetate (3×75 ml). Combined organic layer was dried over sodium sulphate and concentrated under vacuum to afford the crude product which was purified by column chromatography to afford the title product (0.8 g).

Step-3: Synthesis of 3-((oxetan-3-yloxy)methyl)aniline 3-((3-Nitrobenzyl)oxy)oxetane (0.3 g, 1.434 mmol) was taken in methanol (10 ml) and at 0° C., Pd—C(10%, 0.07 g) was added. The reaction mixture was stirred under hydrogen atmosphere at room temperature for 5 hrs. The reaction mixture was filtered through celite and the filtrate was concentrated under vacuum to afford the title product (0.2 gm).

$^1$HNMR (400 MHz, CDCl$_3$): δ 7.12 (t, 1H, J=8 Hz) 6.70-6.52 (m, 3H), 4.60 (bs, 2H), 4.37-4.12 (m, 5H), 3.73 (brs, 2H).

Intermediate xii: (3-aminophenyl)(cyclopropyl)methanone

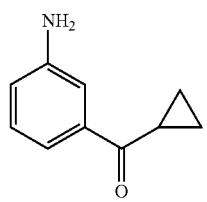 [SMILES: Nc1cccc(C(=O)C2CC2)c1]

Intermediate xiv was prepared using procedure depicted in the reference "Journal of Medicinal Chemistry, 1995, Vol. 38, #18, page 3624-3637".

EXAMPLES

The following examples demonstrate preparation of few representative compounds embodied in formula (I), however, the same should not be construed as limiting the scope of the invention.

Example-1: Synthesis of 1-(3-(cyclopropylsulfonyl) phenyl)-5-((2-fluoro-4-iodo phenyl)amino)-6,8-dimethylpyrido[4,3-d]pyrimidine-2,4,7(1H,3H,6H)-trione (Compound 1)

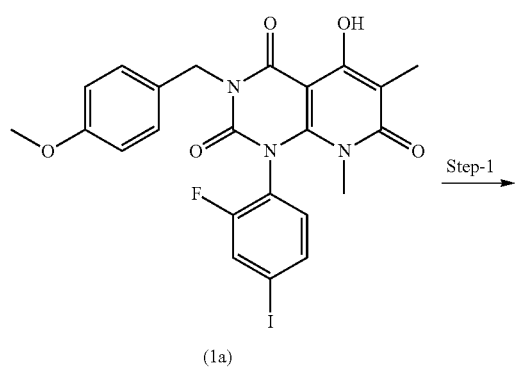

(1a)

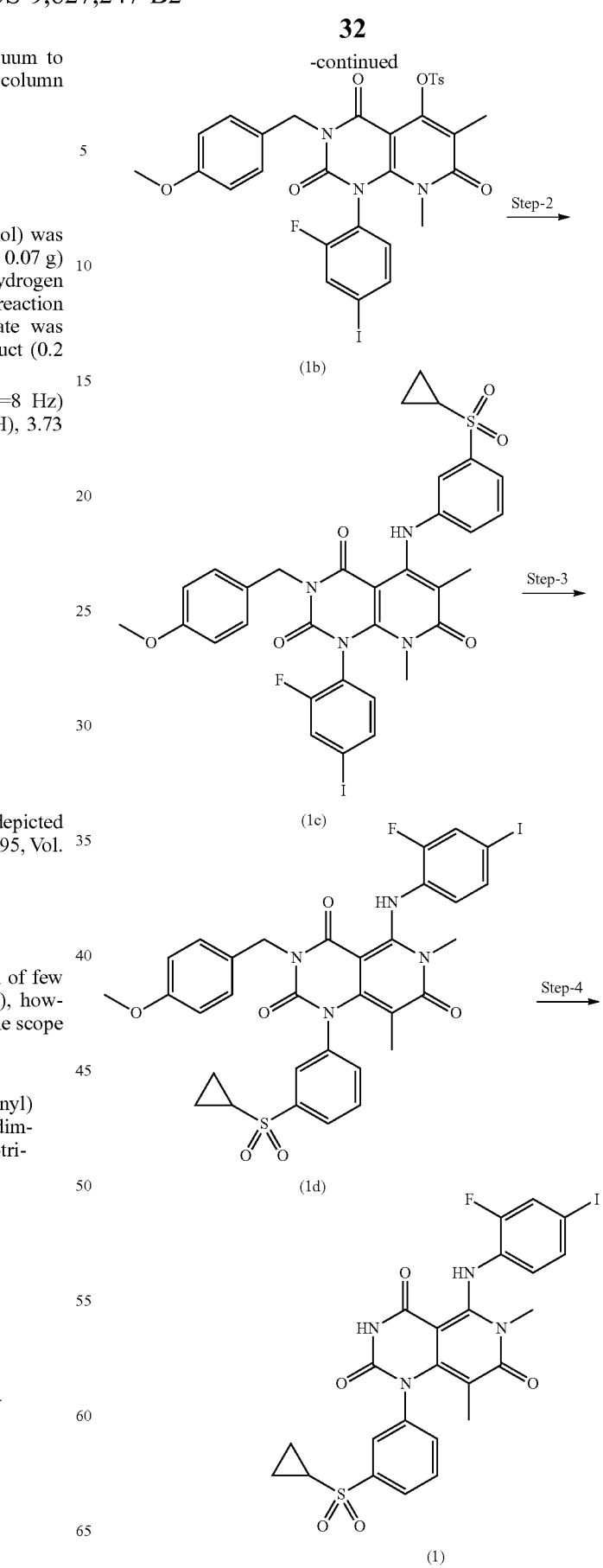

Step-1: Synthesis of 1-(2-fluoro-4-iodophenyl)-3-(4-methoxybenzyl)-6,8-dimethyl-2,4,7-trioxo-1,2,3,4,7,8-hexahydropyrido[2,3-d]pyrimidin-5-yl 4-methylbenzenesulfonate (1b)

Under nitrogen atmosphere, to a solution of 1-(2-fluoro-4-iodophenyl)-5-hydroxy-3-(4-methoxybenzyl)-6,8-dimethylpyrido[2,3-d]pyrimidine-2,4,7(1H,3H,8H)-trione (1a) (41 g, 72.8 mmol) (Prepared as per reference WO2005121142) in acetonitrile (300 ml), triethylamine (30.4 ml, 218 mmol) and trimethylamine hydrochloride (3.48 g, 36.4 mmol) was added dropwise p-toluensulfonylchloride (27.8 g, 146 mmol) in acetonitrile (300 ml) at 0° C., and the mixture was stirred under ice cooling for 1 hr, and at room temperature for 24 h. To the reaction mixture was added methanol (220 ml), and the mixture was stirred at room temperature for 1 h. The precipitated crystals were collected by filtration, dried under vacuum to afford the titled compound (40.5 g, 78%)

$^1$H NMR (400 MHz, DMSO-d$_6$) δ: 7.95 (dd, J=1.6 and 9.6 Hz, 1H), 7.84 (d, J=8.4 Hz, 2H), 7.72 (dd, J=1.2 and 8.4 Hz, 2H), 7.46 (d, J=8.4 Hz, 2H), 7.35 (t, J=8.4 Hz, 1H), 7.23 (d, J=8.8 Hz, 2H), 6.86 (d, J=8.8 Hz, 2H), 4.92 (d, J=16 Hz, 1H), 4.77 (d, J=16 Hz, 1H), 3.71 (s, 3H), 2.76 (s, 3H), 2.42 (s, 3H), 1.53 (s, 3H).

MS: m/z: 717.9

Step-2: Synthesis of 5-((3-(cyclopropylsulfonyl)phenyl)amino)-1-(2-fluoro-4-iodophenyl)-3-(4-methoxybenzyl)-6,8-dimethylpyrido[2,3-d]pyrimidine-2,4,7(1H,3H,8H)-trione (1c)

A mixture of 1-(2-fluoro-4-iodophenyl)-3-(4-methoxybenzyl)-6,8-dimethyl-2,4,7-trioxo-1,2,3,4,7,8-hexahydropyrido[2,3-d]pyrimidin-5-yl 4-methylbenzenesulfonate (1b) (1.0 g, 1.394 mmol), 3-(cyclopropylsulfonyl)aniline (intermediate-i) (1.237 g, 6.27 mmol) and 2,6-LUTIDINE (0.487 ml, 4.18 mmol) in N,N-Dimethylacetamide (0.5 ml) was heated at 140° C. for 18 h in sealed vial. After cooling to rt, the reaction mixture was poured over water (100 ml) and resulting solid was filtered. Residue was purified by flash chromatography on a combiflash instrument to obtain the product.

$^1$HNMR (400 MHz, DMSO-d$_6$) δ (ppm): 10.22 (s, 1H), 7.97 (dd, J=9.2 and 1.6 Hz, 1H), 7.74 (dd, J=8 and 1.2 Hz, 1H), 7.56 (t, J=7.6 Hz, 1H), 7.47 (d, J=8.0 Hz, 1H), 7.38 (t, J=8 Hz, 1H), 7.27-7.33 (m, 4H), 6.83-6.87 (m, 2H), 4.94-5.04 (m, 2H), 3.69 (s, 3H), 2.84-2.87 (m, 1H), 2.78 (s, 3H), 1.55 (s, 3H), 1.02-1.04 (m, 2H), 1.05-1.09 (m, 2H)

MS: m/z: 743.1 [M+1]

Step-3: Synthesis of synthesis of 1-(3-(cyclopropylsulfonyl)phenyl)-5-((2-fluoro-4-iodophenyl)amino)-3-(4-methoxybenzyl)-6,8-dimethylpyrido[4,3-d]pyrimidine-2,4,7(1H,3H,6H)-trione (1d)

Sodium methoxide (25% solution in MeOH) (0.2 ml) was added to a solution of 5-((3-(cyclopropylsulfonyl)phenyl)amino)-1-(2-fluoro-4-iodophenyl)-3-(4-methoxybenzyl)-6,8-dimethylpyrido[2,3-d]pyrimidine-2,4,7(1H,3H,8H)-trione (1c) (0.4 g, 0.539 mmol) in THF (3.5 ml). Resulting solution was stirred under N$_2$ atm for 1 h, and quenched by addition of dil. HCl. Solvents were evaporated in vacuo. and residue was triturated in water. Solid product was filtered and dried under vacuum and used as such for the next step.

$^1$H NMR (400 MHz, DMSO-d$_6$) δ (ppm): 11.09 (s, 1H), 7.88 (brs, 2H), 7.71 (brs, 3H), 7.15 (brs, 3H), 6.81 to 6.83 (d, J=7.2 Hz, 3H), 4.87 (brs, 2H), 3.70 (s, 3H), 3.32 (brs, 3H), 2.88-2.89 (m, 1H), 1.14 (s, 3H), 1.10-1.11 (m, 2H), 1.03-1.05 (d, J=7.4 Hz, 2H)

MS: m/z: 743.1 [M+1].

Step-4: Synthesis of synthesis of 1-(3-(cyclopropylsulfonyl)phenyl)-5-((2-fluoro-4-iodophenyl)amino)-6,8-dimethylpyrido[4,3-d]pyrimidine-2,4,7(1H,3H,6H)-trione (1)

Aluminium chloride (0.628 g, 4.71 mmol) was added to a solution of 1-(3-(cyclopropylsulfonyl)phenyl)-5-((2-fluoro-4-iodophenyl)amino)-3-(4-methoxybenzyl)-6,8-dimethylpyrido[4,3-d]pyrimidine-2,4,7(1H,3H,6H)-trione (1d) (0.350 g, 0.471 mmol) in Anisole (2 ml). Resulting mixture was stirred under N$_2$ atm for 18 h at RT. Reaction was quenched by addition of MeOH. Solvents were evaporated in vacuo. Residue was acidified using dil. HCl. Resulting solid was filtered and heated to reflux in 2-propanol (20 ml) for 1 hr. Reaction mixture was brought to RT and filtered. Residue was purified by flash chromatography to give the pure product.

$^1$HNMR (400 MHz, DMSO-d6), δ 11.66 (s, 1H), 11.20 (s, 1H), 7.93-7.83 (m, 2H), 7.83-7.73 (m, 3H), 7.56 (dd, J=1.2 and 8.4 Hz, 1H), 6.97 (t, J=8.8 Hz, 1H), 3.07 (s, 3H), 2.91-2.87 (m, 1H), 1.16 (s, 3H), 1.15-1.11 (m, 2H), 1.06-1.04 (m, 2H).

Example-2: Synthesis of 3-cyclopropyl-5-((2-fluoro-4-iodophenyl)amino)-1-(3-(3-hydroxyazetidin-1-yl)phenyl)-6,8-dimethylpyrido[4,3-d]pyrimidine-2,4,7(1H,3H,6H)-trione (Compound 2)

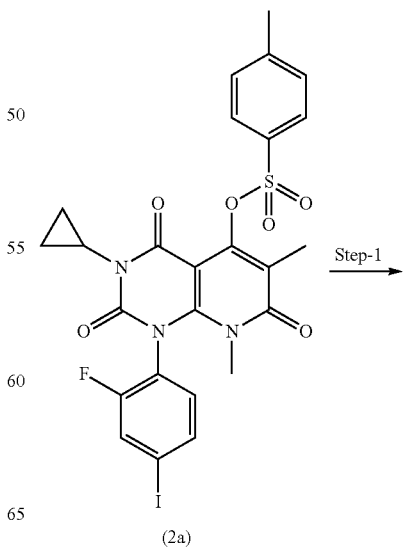

(2a)

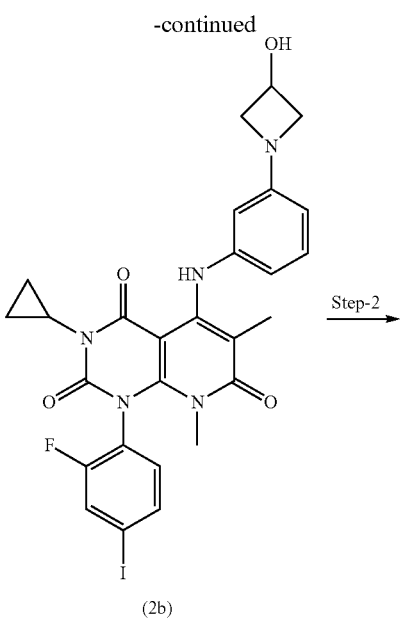

(2b)

(2)

Step-1: Synthesis of 3-cyclopropyl-1-(2-fluoro-4-iodophenyl)-5-((3-(3-hydroxyazetidin-1-yl)phenyl)amino)-6,8-dimethylpyrido[2,3-d]pyrimidine-2,4,7(1H,3H,8H)-trione (2b)

3-cyclopropyl-1-(2-fluoro-4-iodophenyl)-6,8-dimethyl-2,4,7-trioxo-1,2,3,4,7,8-hexahydropyrido[2,3-d]pyrimidin-5-yl 4-methylbenzenesulfonate (2a) (0.5 g, 0.78 mmol), 1-(3-aminophenyl)azetidin-3-ol (vi) (0.13 g, 0.784 mmol) in DMA (1.5 ml), and 2,6-lutidine (0.33 ml, 2.86 mmol) was added in the sealed tube and heated at 130° C. for 10 hr under nitrogen atmosphere. After completion of the reaction, the reaction mixture was poured into ice cold water and extracted with ethyl acetate (2×10 ml). The organic layers were combined, washed with saturated ammonium chloride, water and dried over sodium sulfate. The organic layer was then concentrated under reduced pressure to obtain a crude product which was purified by column chromatography to yield the titled compound (2b) as a white solid (0.09 g, 18%) [MS: m/z=630 (M+1)].

Step-2: Synthesis of 3-cyclopropyl-5-((2-fluoro-4-iodophenyl)amino)-1-(3-(3-hydroxyazetidin-1-yl)phenyl)-6,8-dimethylpyrido[4,3-d]pyrimidine-2,4,7(1H,3H,6H)-trione (2)

3-cyclopropyl-1-(2-fluoro-4-iodophenyl)-5-((3-(3-hydroxyazetidin-1-yl)phenyl)amino)-6,8-dimethylpyrido[2,3-d]pyrimidine-2,4,7(1H,3H,8H)-trione (2b) (0.03 g, 0.048 mmol) was taken in tetrahydrofuran (1 ml) at room temperature, sodium methoxide (30% in MeOH, 23 µL) was added and the reaction mixture was stirred at the same temperature for 2 hr under nitrogen atmosphere. The progress of the reaction was monitored on HPLC. After complete consumption of the substrate, the reaction mixture was concentrated and submitted as such for LCMS and preparative HPLC to yield the titled compound (2) as white solid (0.013 g)

$^1$HNMR (400 MHz, DMSO-d6), δ 11.09 (s, 1H), 7.75 (bs, 1H), 7.53-7.51 (m, 1H), 7.20 (t, 1H), 6.90 (t, 1H), 6.64 (d, 1H, J=8 Hz), 6.43 (d, 2H, J=2 Hz), 5.63 (d, 1H, J=6.4 Hz), 4.56 (bs, 1H), 4.07-4.04 (m, 2H), 3.50-3.47 (m, 2H), 3.07 (s, 3H), 1.29 (s, 3H), 1.09 (t, 1H, J=6.8 Hz), 1.0-0.9 (m, 2H), 0.64-0.62 (m, 2H). MS: m/z=630 (M+1)].

The compounds given below in Table 1: were prepared by procedure similar to the one described above in Example 2 with the above stated intermediates with appropriate variations in reactants, reaction conditions and quantities of reagents.

TABLE 1

| Compound No. | Intermediate No. | IUPAC name | Analytical data |
|---|---|---|---|
| 3 | i | 3-cyclopropyl-1-(3-(cyclopropylsulfonyl)phenyl)-5-((2-fluoro-4-iodophenyl)amino)-6,8-dimethylpyrido[4,3-d]pyrimidine-2,4,7(1H,3H,6H)-trione | $^1$HNMR (400 MHz, DMSO-d6), δ 11.06 (s, 1H), 7.91-7.90 (m, 2H), 7.81-7.73 (m, 3H), 7.57-7.54 (m, 1H), 6.96 (t, J = 8.4 Hz, 1H), 3.09 (s, 3H), 2.91-2.87 (m, 1H), 2.64-2.60 (m, 1H), 1.16 (s, 3H), 1.13-0.86 (m, 6H), 0.69-0.67 (m, 2H). MS: m/z 662.9 (M + 1). |
| 4 | vii | 3-cyclopropyl-5-((2-fluoro-4-iodophenyl)amino)-6,8-dimethyl-1-(3-(2-oxoazetidin-1-yl)phenyl)pyrido[4,3-d]pyrimidine-2,4,7(1H,3H,6H)-trione | $^1$HNMR (400 MHz, DMSO-d6), δ 11.10(s, 1H), 7.9 (dd, 1H, J = 2 and 8.4 Hz), 7.50 (dd, 1H, J = 2 and 8.4 Hz), 7.43-7.41 (m, 2H), 7.33 (d, 1H, J = 6.0 Hz), 7.07 (d, 1H, J = 6.0 Hz), 6.92 (t, 1H, J = 8.6 Hz), 3.65 (t, 2H, J = 4.4 Hz), 3.10-3.07 (m, 5H), 2.63-2.59 (m, 1H), 1.25 (s, 3H), 0.96-0.94 (m, 2H), 0.68-0.66 (m, 2H). MS: m/z 628 (M + 1). |

TABLE 1-continued

| Compound No. | Intermediate No. | IUPAC name | Analytical data |
|---|---|---|---|
| 5 | x | 3-cyclopropyl-5-((2-fluoro-4-iodophenyl)amino)-6,8-dimethyl-1-(3-(oxetan-3-ylamino)phenyl)pyrido[4,3-d]pyrimidine-2,4,7(1H,3H,6H)-trione | $^1$HNMR (400 MHz, DMSO-d6), δ 11.09 (s, 1H), 7.79 (d, 1H, J = 10.4 Hz), 7.55 (d, 1H, J = 8.8 Hz), 7.24 (m, 1H), 6.90 (t, 1H, J = 8.8 Hz), 6.58-6.56 (m, 2H), 6.51-6.50 (m, 1H), 6.47-6.45 (m, 1H), 4.82 (t, 2H, J = 6.4 Hz), 4.55-4.50 (m, 1H), 4.38 (bs, 2H), 3.07 (s, 3H), 2.63-2.55 (m, 1H), 1.3 (s, 3H), 0.95-0.94 (m, 2H), 0.66-0.64 (bs, 2H). MS: m/z 630 (M + 1). |
| 6 | v | tert-butyl 3-((3-(3-cyclopropyl-5-((2-fluoro-4-iodophenyl)amino)-6,8-dimethyl-2,4,7-trioxo-3,4,6,7-tetrahydropyrido[4,3-d]pyrimidin-1(2H)-yl)phenyl)carbamoyl)azetidine-1-carboxylate | MS: m/z 757 (M + 1). |
| 7 | viii | 3-cyclopropyl-5-((2-fluoro-4-iodophenyl)amino)-6,8-dimethyl-1-(3-(oxetan-3-yloxy)phenyl)pyrido[4,3-d]pyrimidine-2,4,7(1H,3H,6H)-trione | $^1$HNMR (400 MHz, DMSO-d6), δ 11.06 (s, 1H), 7.78 (d, 1H, J = 10.8 Hz), 7.54 (d, 1H, J = 8.0 Hz), 7.36 (t, 1H, J = 8.0 Hz), 7.99 (d, 1H, J = 8.0 Hz), 6.95-6.87 (m, 2H), 6.80 (dd, 1H, J = 2.4 and 6.0 Hz), 5.30-5.27 (m, 1H), 4.91 (t, 2H, J = 6.6 Hz), 4.52 (t, 2H, J = 5.8 Hz), 3.08 (s, 3H), 2.61 (bs, 1H), 1.23 (s, 3H), 0.96-0.94 (m, 2H), 0.67-0.65 (m, 2H). MS: m/z 631 (M + 1). |
| 8 | iv | 1-(3-(azetidin-1-yl)phenyl)-3-cyclopropyl-5-((2-fluoro-4-iodophenyl)amino)-6,8-dimethylpyrido[4,3-d]pyrimidine-2,4,7(1H,3H,6H)-trione | MS: m/z 614 (M + 1). |
| 9 | iii | 3-cyclopropyl-5-((2-fluoro-4-iodophenyl)amino)-1-(3-(3-hydroxyoxetan-3-yl)phenyl)-6,8-dimethylpyrido[4,3-d]pyrimidine-2,4,7(1H,3H,6H)-trione | $^1$HNMR (400 MHz, DMSO-d6), δ 11.33 (s, 1H), 7.70 (d, 1H, J = 8 Hz), 7.55-7.46 (m, 3H), 7.31-7.30 (m, 1H), 6.74-6.60 (m, 2H), 4.94-4.86 (m, 4H), 3.21 (s, 3H), 2.78-2.72 (m, 2H), 1.36 (s, 3H), 1.15-1.13 (m, 2H), 0.83-0.81 (m, 2H). MS: m/z 631 (M + 1). |
| 10 | ii | N-(3-(3-cyclopropyl-5-((2-fluoro-4-iodophenyl)amino)-6,8-dimethyl-2,4,7-trioxo-3,4,6,7-tetrahydropyrido[4,3-d]pyrimidin-1(2H)-yl)phenyl)-3-methyloxetane-3-carboxamide | $^1$HNMR (400 MHz, DMSO-d6), δ 11.05 (s, 1H), 9.94 (s, 1H), 7.78 (d, 1H, J = 9.6 Hz), 7.67 (d, 1H, J = 8 Hz), 7.61 (s, 1H), 7.54 (d, 1H, J = 8.4 Hz), 7.38 (t, 1H, J = 7.2 Hz), 7.07 (d, 1H, J = 7.2 Hz), 6.91 (t, 1H, J = 8.4 Hz), 4.82 (d, 2H, J = 6 Hz), 4.33 (d, 2H, J = 6 Hz), 3.07 (s, 3H), 2.60 (m, 1H), 1.60 (s, 3H), 1.27 (s, 3H), 0.97-0.94 (m, 2H), 0.66-0.64 (s, 2H). MS: m/z 672 (M + 1). |
| 11 | xii | 1-(3-(cyclopropanecarbonyl)phenyl)-3-cyclopropyl-5-((2-fluoro-4-iodophenyl)amino)-6,8-dimethylpyrido[4,3-d]pyrimidine-2,4,7(1H,3H,6H)-trione | $^1$HNMR (400 MHz, DMSO-d6), δ 11.08 (s, 1H), 8.12-8.09 (m, 1H), 8.01 (bs, 1H), 7.79 (dd, 1H, J = 2 Hz J = 10.4 Hz), 7.69-7.62 (m, 2H), 7.56-7.54 (m, 1H), 6.94 (t, 1H J = 8.4 Hz), 0.68 (bs, 2H), 3.07 (s, 3H), 2.90 (m, 1H), 2.61-2.60 (m, 1H), 1.18 (s, 3H), 1.06-1.08 (m, 4H), 0.96-0.95 (m, 2H). MS: m/z 627.1 (M + 1). |
| 12 | i | 1-(3-(cyclopropylsulfonyl)phenyl)-5-((2-fluoro-4-iodophenyl)amino)-3,6,8-trimethylpyrido[4,3-d]pyrimidine-2,4,7(1H,3H,6H)-trione | $^1$HNMR (400 MHz, DMSO-d6), δ 11.18 (s, 1H), 7.94-7.92 (m, 2H), 7.84-7.45 (m, 3H), 6.96 (t, J = 8.8 Hz, 1H), 3.22 (s, 3H), 3.09 (s, 3H), 1.78-1.74 (m, 1H), 1.18 (s, 3H), 1.13-1.12 (m, 2H), 1.07-1.05 (m, 2H). MS: m/z 637 (M + 1). |

TABLE 1-continued

| Compound No. | Intermediate No. | IUPAC name | Analytical data |
|---|---|---|---|
| 13 | xi | 5-((2-fluoro-4-iodophenyl)amino)-3,6,8-trimethyl-1-(3-((oxetan-3-yloxy)methyl)phenyl)pyrido[4,3-d]pyrimidine-2,4,7(1H,3H,6H)-trione | $^1$HNMR (400 MHz, DMSO-d6), δ 11.20 (s, 1H), 7.79 (dd, 1H, J = 2 and 8 Hz), 7.55 (d, 1H, J = 8.4 Hz), 7.47-7.43 (m, 1H), 7.39-7.33 (m, 3H), 6.93 (t, 1H, J = 8.4 Hz), 4.63-4.60 (m, 3H), 4.69 (s, 2H), 4.42-4.41 (m, 2H), 3.21 (s, 3H), 3.08 (s, 3H), 1.19 (s, 3H). MS: m/z 619 (M + 1). |
| 14 | iii | 5-((2-fluoro-4-iodophenyl)amino)-1-(3-(3-hydroxyoxetan-3-yl)phenyl)-3,6,8-trimethylpyrido[4,3-d]pyrimidine-2,4,7(1H,3H,6H)-trione | $^1$HNMR (400 MHz, DMSO-d6), δ 11.22 (s, 1H), 7.79 (dd, 1H, J = 10 and 1.6 Hz), 7.66 (d, 1H, J = 8 Hz), 7.58-7.48 (m, 3H), 7.36 (dd, 1H, J = 8.8 and 1.2 Hz), 6.93 (t, 1H, J = 8.8 Hz), 4.78 (d, 2H, J = 6.4 Hz), 4.65 (bs, 2H), 3.20 (s, 3H), 2.60 (bs, 1H), 3.08 (s, 3H), 1.19 (s, 3H). MS: m/z 605 (M + 1). |
| 15 | viii | 5-((2-fluoro-4-iodophenyl)amino)-3,6,8-trimethyl-1-(3-(oxetan-3-yloxy)phenyl)pyrido[4,3-d]pyrimidine-2,4,7(1H,3H,6H)-trione | $^1$HNMR (400 MHz, DMSO-d6), δ 11.19 (s, 1H), 7.79 (dd, 1H, J = 2 and 8.4 Hz), 7.55 (d, 1H, J = 8.4 Hz), 7.37 (t, 1H, J = 8.0 Hz), 7.02 (dd, 1H, J = 1.2 and 6.8 Hz), 6.96-6.91 (m, 2H), 6.86 (dd, 1H, J = 2 and 8.4 Hz), 5.32-5.27 (m, 1H), 4.91 (t, 2H, J = 6.8 Hz), 4.52 (t, 2H, J = 6.0 Hz), 3.21 (s, 3H), 3.08 (s, 3H), 1.24 (s, 3H). MS: m/z 604 (M + 1). |
| 16 | iv | 1-(3-(azetidin-1-yl)phenyl)-5-((2-fluoro-4-iodophenyl)amino)-3,6,8-trimethylpyrido[4,3-d]pyrimidine-2,4,7(1H,3H,6H)-trione | $^1$HNMR (400 MHz, CDCl$_3$), δ 11.45 (s, 1H), 7.53 (dd, 1H, J = 2 and 10 Hz), 7.45(d, 1H, J = 8.4), 7.22 (t, 1H, J = 8 Hz), 6.70-6.63 (m, 3H), 6.56-6.55 (m, 1H), 3.66 (t, 2H, J = 6.4 Hz), 3.39 (s, 3H), 3.34 (t, 2H, J = 6.8 Hz), 3.23(s, 3H), 2.10-2.04 (m, 2H), 1.5 (s, 3H). MS: m/z 588 (M + 1). |
| 17 | x | 5-((2-fluoro-4-iodophenyl)amino)-3,6,8-trimethyl-1-(3-(oxetan-3-ylamino)phenyl)pyrido[4,3-d]pyrimidine-2,4,7(1H,3H,6H)-trione | $^1$HNMR (400 MHz, DMSO-d6), δ 11.22 (s, 1H), 7.79 (dd, 1H, J = 2 and 12 Hz), 7.55 (d, 1H, J = 8.4), 7.15 (t, 1H, J = 8 Hz), 6.91 (t, 1H, J = 8.8 Hz), 6.59 (d, 2H, J = 6.8), 6.49 (d, 2H, J = 8 Hz), 4.82 (t, 2H, J = 6.4), 4.54-4.50 (m, 1H), 4.40-4.37 (m, 2H), 3.2 (s, 3H), 3.07(s, 3H), 1.32 (s, 3H). MS: m/z 604 (M + 1). |
| 18 | ii | N-(3-(5-((2-fluoro-4-iodophenyl)amino)-3,6,8-trimethyl-2,4,7-trioxo-3,4,6,7-tetrahydropyrido[4,3-d]pyrimidin-1(2H)-yl)phenyl)-3-methyloxetane-3-carboxamide | $^1$HNMR (400 MHz, DMSO-d6), δ 11.18 (s, 1H), 9.93 (s, 1H), 7.78 (d, 1H, J = 8.8 Hz) 7.67 (s, 1H), 7.64 (d, 1H, J = 8 Hz), 7.54 (d, 1H, J = 8.8 Hz), 7.40 (t, 1H, J = 8 Hz), 7.11 (dd, 1H, J = 1.2 and 8 Hz), 6.93 (t, 1H, J = 8.8 Hz), 4.82 (d, 2H, J = 6 Hz), 4.33 (d, 2H, J = 6 Hz), 3.2 (s, 3H), 3.08 (s, 3H), 1.60 (s, 3H), 1.28 (s, 3H). MS: m/z 646 (M + 1). |
| 19 | ix | 2-((1-(3-(5-((2-fluoro-4-iodophenyl)amino)-3,6,8-trimethyl-2,4,7-trioxo-3,4,6,7-tetrahydropyrido[4,3-d]pyrimidin-1(2H)-yl)phenyl)azetidin-3-yl)oxy)acetamide | $^1$HNMR (400 MHz, DMSO-d6), δ 11.24 (s, 1H), 7.77 (d, 1H, J = 9.6 Hz), 7.53 (d, 1H, J = 8 Hz), 7.33 (s, 1H), 7.26-7.21 (m, 2H), 6.91(t, 1H, J = 8.4 Hz), 6.68 (d, 1H, J = 8.4), 6.48-6.46 (m, 2H), 4.47 (m, 1H), 4.06-4.02 (m, 2H), 3.82 (s, 2H), 3.68-3.65 (m, 2H), 3.19 (s, 3H), 3.08 (s, 3H), 1.31 (s, 3H). MS: m/z 661 (M + 1). |

Example 3: Synthesis of 5-((2-fluoro-4-iodophenyl)amino)-1-(3-(3-fluorooxetan-3-yl)phenyl)-3,6,8-trimethylpyrido[4,3-d]pyrimidine-2,4,7(1H,3H,6H)-trione (Compound 20)

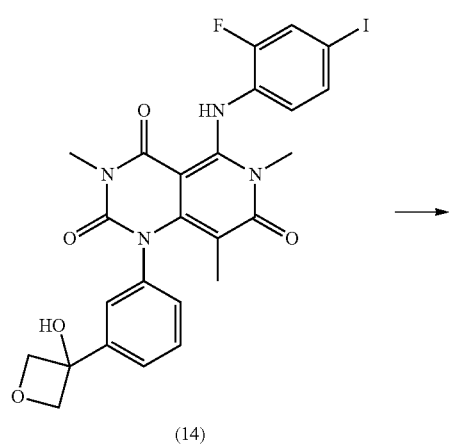

To a solution of 5-((2-Fluoro-4-iodophenyl)amino)-1-(3-(3-hydroxyoxetan-3-yl)phenyl)-3,6,8-trimethylpyrido[4,3-d]pyrimidine-2,4,7(1H,3H,6H)-trione (compound 14) (0.02 g, 0.033 mmol) in DCM (7 ml), DAST (0.017 ml, 0.132 mmol) was added at −78° C., the reaction mixture was stirred at room temperature for 1 hr. Reaction mixture was concentrated and crude compound was purified by column chromatography over silica gel using ethyl acetate (40%) in hexane as eluent. Obtained solid was triturated in diethyl ether to afford the titled compound (0.012 g).

$^1$HNMR (400 MHz, DMSO-d6), δ 11.21 (s, 1H), 7.79 (dd, 1H, J=2.0 and 8.4 Hz), 7.63-7.59 (m, 3H), 7.55 (d, 1H, J=10) 7.49 (d, 1H, J=7.6 Hz), 6.94 (t, 1H, J=8.8 Hz), 5.02-4.87 (m, 4H), 3.21 (s, 3H), 3.08 (s, 3H), 1.19 (s, 3H). ESI-MS: [m/z=607 (M+1)].

Example 4: Synthesis of N-(3-(3-cyclopropyl-5-((2-fluoro-4-iodophenyl)amino)-6,8-dimethyl-2,4,7-trioxo-3,4,6,7-tetrahydropyrido[4,3-d]pyrimidin-1(2H)-yl)phenyl)azetidine-3-carboxamide (21)

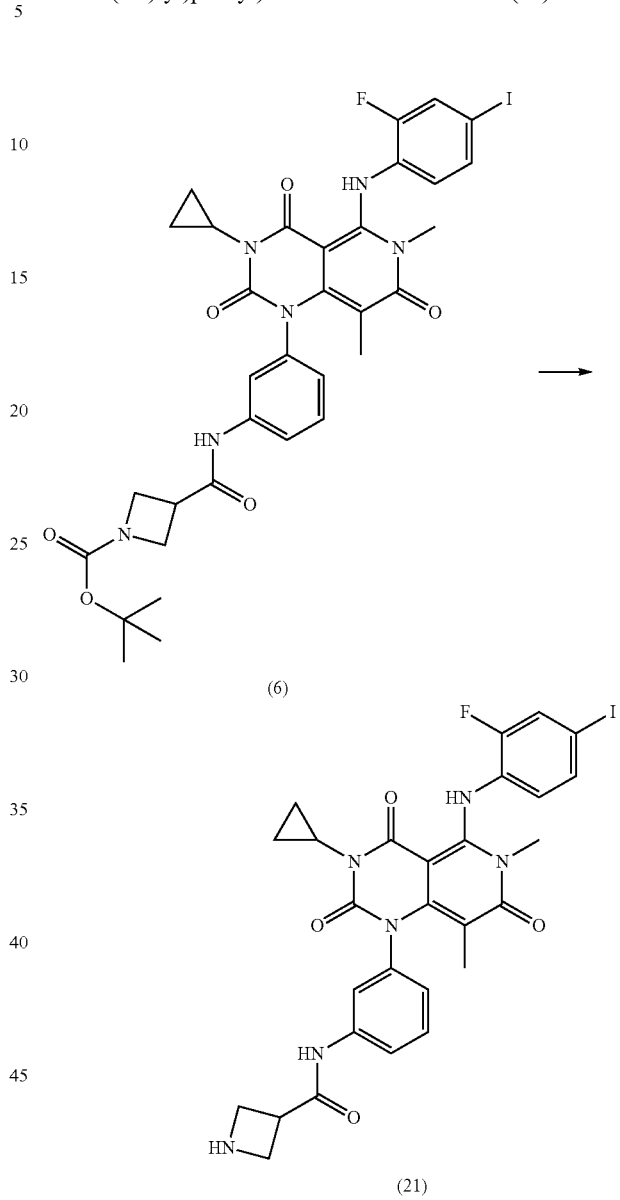

To a solution of tert-butyl 3-((3-(3-cyclopropyl-5-((2-fluoro-4-iodophenyl)amino)-6,8-dimethyl-2,4,7-trioxo-3,4,6,7-tetrahydropyrido[4,3-d]pyrimidin-1(2H)-yl)phenyl) carbamoyl)azetidine-1-carboxylate (compound 6) (0.075 g, 0.099 mmol) in DCM (5.0 ml), TFA (0.038 ml, 0.496 mmol) was added at 0° C. Reaction mixture was stirred at room temperature for 15 hrs, treated with satd. aq. NaHCO$_3$ and the resulting mixture was extracted with DCM (3×10 ml). The combined organic layers were washed with water, brine and dried over sodium sulfate. The organic layer was concentrated under vacuum to obtain a crude product which was triturated in diethyl ether to afford titled compound (0.03 g).

$^1$HNMR (400 MHz, DMSO-d6), δ 11.07 (s, 1H), 10.32 (s, 1H), 8.67 (bs, 1H), 7.81-7.80 (dd, 1H, J=10.4 and 1.6 Hz), 7.65-7.63 (m, 1H), 7.57-7.55 (d, 1H), 7.44-7.39 (m, 1H), 7.09-7.07 (d, 1H, J=6.4 Hz), 6.94-6.90 (t, 1H, J=8.8 Hz), 4.81-4.79 (d, 1H, J=8.8 Hz), 4.10-4.09 (m, 1H), 3.76-3.72 (m, 1H), 3.07 (s, 3H), 2.67-2.60 (m, 2H), 2.33-2.27 (m, 2H), 1.25 (s, 3H), 0.66 (bs, 2H), 0.96-0.94 (m, 2H). ESI-MS: [m/z=657 (M+1)]

Pharmacological Activity

Protocol for In-Vitro Experiments

Example-A: Identification of Compounds Inhibiting MEK Kinase Activity

In a 25 µL reaction, MEK enzyme (final concentration 2-4 µg/ml), and ERK substrate (final concentration 50-100 µg/ml), were incubated with various concentration of test compounds (diluted such that the reaction had 1% DMSO), at 25-30° C. for 20 to 120 min on a shaker incubator. The reactions were initiated by the addition of ATP. The reactions were terminated by adding an equal volume of KinaseGlo reagent (Promega), following the manufacturer's instructions. The plates were read on a luminometer. $IC_{50}$ calculations were done using GraphPad Prism 5.

The Compounds of the invention exhibited $IC_{50}$ values ranging between 1 nM to 600 nM in MEK inhibition assay.

Compound No's 1, 5, 7, 10, 11, 12, 13, 14, 15, 16, 18 and 19 exhibited $IC_{50}$ values in the range 1 to 600 nM.

Example-B: Analysis of ERK Phosphorylation

This assay was carried out with human melanoma cells, human and mouse colon cancer cells. Cells were treated for 1 h with various concentrations of test compounds. ERK phosphorylation analysis was performed using the Alphascreen SureFire Phospho-ERK 1/2 Kit (Perkin Elmer), by following the manufacturer's instructions. % inhibition of ERK phosphorylation was determined as:

100−{(RFU test−RFU lysis buffer control)/(RFU vehicle treated control−RFU lysis buffer control)}×100.

The compounds prepared were tested using the above assay procedure and the results obtained are given in Table 2. Percentage inhibition at concentrations of pERK at 100 nM, 10 nM, 1 nM for the stated examples is setworth here. The percentage inhibition at the above depicted concentrations for the compounds stated are given in the following groups.

Group-A: Compounds having 50-100% inhibition at 1 nM.
Group-B: Compounds having 50-100% inhibition at 10 nM
Group-C: Compounds having 50-100% inhibition at 100 nM.

TABLE 2

| Group | Compounds |
|---|---|
| A | 1, 8, 11, 12, 14, 15, and 17 |
| B | 2, 4, 5, 10, 13, 18, 19 and 20 |
| C | 3, 7, 9, 16 and 21 |

The invention claimed is:

1. A method for inhibiting an MEK kinase, said method comprising: administering a composition to an individual in need of said inhibiting; wherein the composition comprises an effective amount of a compound of formula I and optionally one or more pharmaceutically acceptable carriers, diluents, or excipients; and wherein the compound of formula I is represented by the following structure

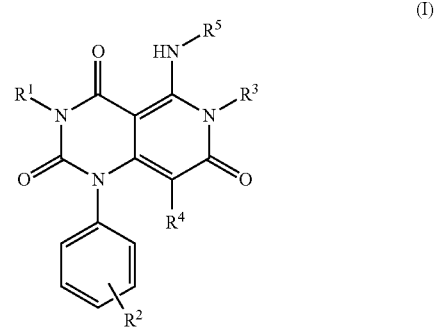

wherein,
$R^1$ is selected from the group consisting of hydrogen, substituted- or unsubstituted-alkyl, substituted- or unsubstituted-cycloalkyl, and substituted- or unsubstituted-heterocyclyl;
$R^2$ is selected from the group consisting of —$R^6$-E, —$SO_2R^7$, and —C(O)$R^8$;
$R^3$ is selected from the group consisting of hydrogen, substituted- or unsubstituted-alkyl, and substituted- or unsubstituted-cycloalkyl;
$R^4$ is selected from the group consisting of hydrogen, halogen, substituted- or unsubstituted-alkyl, and substituted- or unsubstituted-cycloalkyl;
$R^5$ is substituted- or unsubstituted-aryl, wherein the substituents are selected from with $R^a$ and $R^b$;
$R^a$ and $R^b$ are selected from the group consisting of hydrogen, halogen, and haloalkyl;
$R^6$ is selected from the group consisting of direct bond, —[C($R^c$)$R^d$]N$R^9$—, —[C($R^c$)$R^d$]$_n$O—, —NHC(=O)[C($R^c$)$R^d$]$_p$—, —S(O)$_2$NH—, —NHC(=O)[C$R^c$($R^d$)]N$R^9$—, —NHC(=O)[C$R^c$($R^d$)]O—, and —NHS(O)$_2$—;
$R^c$ and $R^d$ are each independently selected from the group consisting of hydrogen and substituted- or unsubstituted-alkyl;
E is substituted- or unsubstituted-four membered heterocyclic ring, wherein the substituents are selected from the group consisting of alkyl, halogen, —C(=O)O$R^e$, and —O$R^e$;
$R^e$ is selected from the group consisting of hydrogen, substituted- or unsubstituted-alkyl, and substituted or unsubstituted cycloalkyl;
$R^7$ is selected from the group consisting of substituted- or unsubstituted-cycloalkyl, and substituted- or unsubstituted-cycloalkenyl;
$R^8$ is selected from the group consisting of substituted- or unsubstituted-alkyl, substituted- or unsubstituted-alkenyl, substituted- or unsubstituted-alkynyl, substituted- or unsubstituted-cycloalkyl, and substituted- or unsubstituted-cycloalkenyl;
$R^9$ is selected from the group consisting of hydrogen, substituted- or unsubstituted-alkyl, substituted- or unsubstituted-alkenyl, substituted- or unsubstituted-alkynyl, substituted- or unsubstituted-cycloalkyl, and substituted- or unsubstituted-cycloalkenyl;
n is an integer selected from the group consisting of 0, 1, and 2;

p is an integer selected from the group consisting of 0 and 1;

when the alkyl group and alkenyl group is substituted, the alkyl group and alkenyl group is substituted with 1 to 4 substituents independently selected from the group consisting of oxo, halogen, nitro, cyano, perhaloalkyl, cycloalkyl, aryl, heteroaryl, heterocyclyl, —OR$^{10b}$, —SO$_2$R$^{10a}$, —C(=O)R$^{10a}$, —OC(=O)R$^{10a}$, —C(=O)N(H)R$^{10}$, —OR$^{10a}$, —C(=O)N(alkyl)R$^{10}$, —N(H)C(=O)R$^{10a}$, —N(H)R$^{10}$, —N(alkyl)R$^{10}$—N(H)C(=O)N(H)R$^{10}$, —N(H)C(=O)N(alkyl)R$^{10}$, —NH—SO$_2$-alkyl, and —NH—SO$_2$-cycloalkyl;

when the cycloalkyl group and cycloalkenyl group is substituted, the cycloalkyl group and cycloalkenyl group is substituted with 1 to 3 substituents independently selected from the group consisting of oxo, halogen, nitro, cyano, alkyl, alkenyl, perhaloalkyl, aryl, heteroaryl, heterocyclyl, —OR$^{10b}$, —SO$_2$R$^{10a}$, —C(=O)R$^{10a}$, —C(=O)OR$^{10a}$, —OC(=O)R$^{10a}$, —C(=O)N(H)R$^{10}$, —C(=O)N(alkyl)R$^{10}$, —N(H)C(=O)R$^{10a}$, —N(H)R$^{10}$, —N(alkyl)R$^{10}$, —N(H)C(=O)N(H)R$^{10}$, —N(H)C(=O)N(alkyl)R$^{10}$, —NH—SO$_2$-alkyl, and —NH—SO$_2$-cycloalkyl;

when the aryl group is substituted, the aryl group is substituted with 1 to 3 substituents independently selected from the group consisting of halogen, nitro, cyano, hydroxy, alkyl, alkenyl, perhaloalkyl, cycloalkyl, cycloalkenyl, heterocycle, —O-alkyl, —O-perhaloalkyl, —N(alkyl)alkyl, —N(H)alkyl, —NH$_2$, —SO$_2$-alkyl, —SO$_2$-perhaloalkyl, —N(alkyl)C(=O)alkyl, —N(H)C(=O)alkyl, —C(=O)N(alkyl)alkyl, —C(=O)N(H)alkyl, —C(=O)NH$_2$, —SO$_2$N(alkyl)alkyl, —SO$_2$N(H)alkyl, —SO$_2$NH$_2$, —NH—SO$_2$-alkyl, and —NH—SO$_2$-cycloalkyl;

when the heteroaryl group is substituted, the heteroaryl group is substituted with 1 to 3 substituents independently selected from the group consisting of halogen, nitro, cyano, hydroxy, alkyl, alkenyl, perhaloalkyl, cycloalkyl, cycloalkenyl, heterocycle, —O-alkyl, —O-perhaloalkyl, —N(alkyl)alkyl, —N(H)alkyl, —NH$_2$, —SO$_2$-alkyl, —SO$_2$-perhaloalkyl, —N(alkyl)C(=O)alkyl, —N(H)C(=O)alkyl, —C(=O)N(alkyl)alkyl, —C(=O)N(H)alkyl, —C(=O)NH$_2$, —SO$_2$N(alkyl)alkyl, —SO$_2$N(H)alkyl, —SO$_2$NH$_2$, —NH—SO$_2$-alkyl, and —NH—SO$_2$-cycloalkyl;

when the heterocyclyl group is substituted, the heterocyclyl group is substituted with 1 to 3 substituents, when the heterocyclic group is substituted on a ring carbon of the 'heterocycle', the substituents are independently selected from the group consisting of halogen, nitro, cyano, oxo, alkyl, alkenyl, perhaloalkyl, cycloalkyl, cycloalkenyl, aryl, heteroaryl, heterocyclyl, —OR$^{10b}$, —C(=O)OR$^{10a}$, —OC(=O)R$^{10a}$, —C(=O)N(H)R$_{10}$, —C(=O)N(alkyl)R$^{10}$, —N(H)C(=O)R$^{10a}$, —N(H)R$^{10}$, —N(alkyl)R$^{10}$, —N(H)C(=O)N(H)R$^{10}$, and —N(H)C(=O)N(alkyl)R$^{10}$;

when the heterocyclic group is substituted on a ring nitrogen of the 'heterocycle', substituents are independently selected from the group consisting of alkyl, alkenyl, cycloalkyl, cycloalkenyl, aryl, heteroaryl, —SO$_2$R$^{10a}$, —C(=O)R$^{10a}$, C(=O)OR$^{10a}$, —C(=O)N(H)R$^{10}$, —C(=O)N(alkyl)R$^{10}$, —NH—SO$_2$-alkyl, and —NH—SO$_2$-cycloalkyl;

R$^{10}$ is selected from the group consisting of hydrogen, alkyl, alkenyl, cycloalkyl, cycloalkenyl, aryl, heteroaryl, and heterocyclyl;

R$^{10a}$ is selected from the group consisting of alkyl, alkenyl, perhaloalkyl, cycloalkyl, cycloalkenyl, aryl, heteroaryl, and heterocyclyl; and R$^{10b}$ is selected from the group consisting of hydrogen, alkyl, alkenyl, perhaloalkyl, cycloalkyl, cycloalkenyl, aryl, heteroaryl, and heterocyclyl;

wherein the compound of formula I includes a tautomeric form thereof, a stereoisomeric form thereof, or a pharmaceutically acceptable salt thereof.

2. A method for inhibiting an MEK kinase, said method comprising:

administering a composition to an individual in need of said inhibiting; wherein the composition comprises an effective amount of a compound of formula Ia and optionally one or more pharmaceutically acceptable carriers, diluents, or excipients; and wherein the compound of formula Ia is represented by the following structure

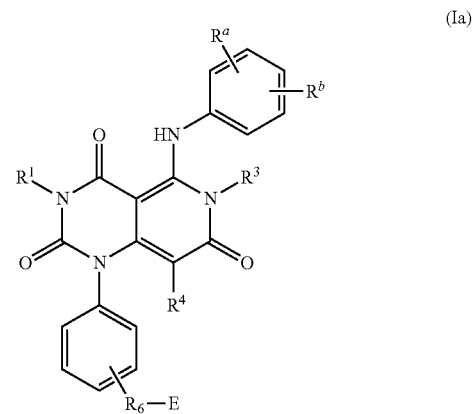

(Ia)

wherein,

R$^1$ is selected from the group consisting of hydrogen, substituted- or unsubstituted-alkyl, substituted- or unsubstituted-cycloalkyl, and substituted- or unsubstituted-heterocyclyl;

R$^3$ is selected from the group consisting of hydrogen, substituted- or unsubstituted-alkyl, and substituted- or unsubstituted-cycloalkyl;

R$^4$ is selected from the group consisting of hydrogen, halogen, substituted- or unsubstituted-alkyl, and substituted- or unsubstituted-cycloalkyl;

R$^a$ and R$^b$ are selected from the group consisting of hydrogen, halogen, and haloalkyl;

R$^6$ is selected from the group consisting of direct bond, —[C(R$^c$)R$^d$]NR$^9$—, —[C(R$^c$)R$^d$]$_n$O—, —NHC(=O)[C(R$^c$)R$^d$], —S(O)$_2$NH—, —NHC(=O)[CR$^c$(R$^d$)]NR$^9$, —NHC(=O)[CR$^c$(R$^d$)]O—, and —NHS(O)$_2$—;

R$^c$ and R$^d$ are each independently selected from the group consisting of hydrogen and substituted- or unsubstituted-alkyl;

E is substituted- or unsubstituted-four membered heterocyclic ring, wherein the substituents are selected from the group consisting of alkyl, halogen, —C(=O)OR$^e$, and —OR$^e$;

R$^e$ is selected from the group consisting of hydrogen, substituted- or unsubstituted-alkyl, and substituted or unsubstituted cycloalkyl;

R$^9$ is selected from the group consisting of hydrogen, substituted- or unsubstituted-alkyl, substituted- or unsubstituted-alkenyl, substituted- or unsubstituted-alkynyl, substituted- or unsubstituted-cycloalkyl and substituted- or unsubstituted-cycloalkenyl;

n is an integer selected from the group consisting of 0, 1, and 2;

p is an integer selected from the group consisting of 0 and 1;

when the alkyl group and alkenyl group is substituted, the alkyl group and alkenyl group is substituted with 1 to 4 substituents independently selected from the group consisting of oxo, halogen, nitro, cyano, perhaloalkyl, cycloalkyl, aryl, heteroaryl, heterocyclyl, —OR$^{10b}$, —SO$_2$R$^{10a}$, —C(=O)OR$^{10a}$, —OC(=O)R$^{10a}$, —C(=O)N(H)R$^{10}$, —OR$^{10a}$, —C(=O)N(alkyl)R$^{10}$, —N(H)C(=O)R$^{10a}$, —N(H)R$^{10}$, —N(alkyl)R$^{10}$—N(H)C(=O)N(H)R$^{10}$, —N(H)C(=O)N(alkyl)R$^{10}$, —NH—SO$_2$-alkyl, and —NH—SO$_2$-cycloalkyl;

when the cycloalkyl group and cycloalkenyl group is substituted, the cycloalkyl group and cycloalkenyl group is substituted with 1 to 3 substituents independently selected from the group consisting of oxo, halogen, nitro, cyano, alkyl, alkenyl, perhaloalkyl, aryl, heteroaryl, heterocyclyl, —OR$^{10b}$, —SO$_2$R$^{10a}$, —C(=O)R$^{10a}$, —C(=O)OR$^{10a}$, —OC(=O)R$^{10a}$, —C(=O)N(H)R$^{10}$, —C(=O)N(alkyl)R$^{10}$, —N(H)C(=O)R$^{10a}$, —N(H)R$^{10}$, —N(alkyl)R$^{10}$, —N(H)C(=O)N(H)R$^{10}$, —N(H)C(=O)N(alkyl)R$^{10}$, —NH—SO$_2$-alkyl, and —NH—SO$_2$-cycloalkyl;

when the aryl group is substituted, the aryl group is substituted with 1 to 3 substituents independently selected from the group consisting of halogen, nitro, cyano, hydroxy, alkyl, alkenyl, perhaloalkyl, cycloalkyl, cycloalkenyl, heterocycle, —O-alkyl, —O-perhaloalkyl, —N(alkyl)alkyl, —N(H)alkyl, —NH$_2$, —SO$_2$-alkyl, —SO$_2$-perhaloalkyl, —N(alkyl)C(=O)alkyl, —N(H)C(=O)alkyl, —C(=O)N(alkyl)alkyl, —C(=O)N(H)alkyl, —C(=O)NH$_2$, —SO$_2$N(alkyl)alkyl, —SO$_2$N(H)alkyl, —SO$_2$NH$_2$, —NH—SO$_2$-alkyl, and —NH—SO$_2$-cycloalkyl;

when the heteroaryl group is substituted, the heteroaryl group is substituted with 1 to 3 substituents independently selected from the group consisting of halogen, nitro, cyano, hydroxy, alkyl, alkenyl, perhaloalkyl, cycloalkyl, cycloalkenyl, heterocycle, —O-alkyl, —O-perhaloalkyl, —N(alkyl)alkyl, —N(H)alkyl, —NH$_2$, —SO$_2$-alkyl, —SO$_2$-perhaloalkyl, —N(alkyl)C(=O)alkyl, —N(H)C(=O)alkyl, —C(=O)N(alkyl)alkyl, —C(=O)N(H)alkyl, —C(=O)NH$_2$, —SO$_2$N(alkyl)alkyl, —SO$_2$N(H)alkyl, —SO$_2$NH$_2$, —NH—SO$_2$-alkyl, and —NH—SO$_2$-cycloalkyl;

when the heterocyclyl group is substituted, the heterocyclyl group is substituted with 1 to 3 substituents, when the heterocyclic group is substituted on a ring carbon of the 'heterocycle', the substituents are independently selected from the group consisting of halogen, nitro, cyano, oxo, alkyl, alkenyl, perhaloalkyl, cycloalkyl, cycloalkenyl, aryl, heteroaryl, heterocyclyl, —OR$^{10b}$, —C(=O)OR$^{10a}$, —OC(=O)R$^{10a}$, —C(=O)N(H)R$^{10}$, —C(=O)N(alkyl)R$^{10}$, —N(H)C(=O)R$^{10a}$, —N(H)R$^{10}$, —N(alkyl)R$^{10}$, —N(H)C(=O)N(H)R$^{10}$, and —N(H)C(=O)N(alkyl)R$^{10}$;

when the heterocyclic group is substituted on a ring nitrogen of the 'heterocycle', substituents are independently selected from the group consisting of alkyl, alkenyl, cycloalkyl, cycloalkenyl, aryl, heteroaryl, —SO$_2$R$^{10a}$, —C(=O)R$^{10a}$, C(=O)OR$^{10a}$, —C(=O)N(H)R$^{10}$, —C(=O)N(alkyl)R$^{10}$, —NH—SO$_2$-alkyl, and —NH—SO$_2$-cycloalkyl;

R$^{10}$ is selected from the group consisting of hydrogen, alkyl, alkenyl, cycloalkyl, cycloalkenyl, aryl, heteroaryl, and heterocyclyl;

R$^{10a}$ is selected from the group consisting of alkyl, alkenyl, perhaloalkyl, cycloalkyl, cycloalkenyl, aryl, heteroaryl, and heterocyclyl; and R$^{10b}$ is selected from the group consisting of hydrogen, alkyl, alkenyl, perhaloalkyl, cycloalkyl, cycloalkenyl, aryl, heteroaryl, and heterocyclyl;

wherein the compound of formula Ia includes a tautomeric form thereof, a stereoisomeric form thereof, or a pharmaceutically acceptable salt thereof.

3. A method for inhibiting an MEK kinase, said method comprising:

administering a composition to an individual in need of said inhibiting; wherein the composition comprises an effective amount of a compound of formula Ib and optionally one or more pharmaceutically acceptable carriers, diluents, or excipients; and wherein the compound of formula I is represented by the following structure (Ib)

wherein,

R$^1$ is selected from the group consisting of hydrogen, substituted- or unsubstituted-alkyl, substituted- or unsubstituted-cycloalkyl, and substituted- or unsubstituted-heterocyclyl;

R$^3$ is selected from the group consisting of hydrogen, substituted- or unsubstituted-alkyl, and substituted- or unsubstituted-cycloalkyl;

R$^4$ is selected from the group consisting of hydrogen, halogen, substituted- or unsubstituted-alkyl, and substituted- or unsubstituted-cycloalkyl;

R$^a$ and R$^b$ are selected from the group consisting of hydrogen, halogen and haloalkyl;

R$^7$ is selected from the group consisting of substituted- or unsubstituted-cycloalkyl, and substituted- or unsubstituted-cycloalkenyl;

when the alkyl group and alkenyl group is substituted, the alkyl group and alkenyl group is substituted with 1 to 4 substituents independently selected from the group consisting of oxo, halogen, nitro, cyano, perhaloalkyl, cycloalkyl, aryl, heteroaryl, heterocyclyl, —OR$^{10b}$, —SO$_2$R$^{10a}$, —C(=O)OR$^{10a}$, —OC(=O)R$^{10a}$, —C(=O)N(H)R$^{10}$, —OR$^{10a}$, —C(=O)N(alkyl)R$^{10}$, —N(H)C(=O)R$^{10a}$, —N(H)R$^{10}$, —N(alkyl)R$^{10}$—N (H)C(=O)N(H)R$^{10}$, —N(H)C(=O)N(alkyl)R$^1$, —NH—SO$_2$-alkyl, and —NH—SO$_2$-cycloalkyl;

when the cycloalkyl group and cycloalkenyl group is substituted, the cycloalkyl group and cycloalkenyl group is substituted with 1 to 3 substituents independently selected from the group consisting of oxo, halogen, nitro, cyano, alkyl, alkenyl, perhaloalkyl, aryl, heteroaryl, heterocyclyl, —OR$^{10b}$, —SO$_2$R$^{10a}$, —C(=O)R$^{10a}$, —C(=O)OR$^{10a}$, —OC(=O)R$^{10a}$, —C(=O)N(H)R$^{10}$, —C(=O)N(alkyl)R$^1$, —N(H)C(=O)R$^{10a}$, —N(H)R$^{10}$, —N(alkyl)R$^{10}$, —N(H)C(=O)N(H)R$^{10}$, —N(H)C(=O)N(alkyl)R$^{10}$, —NH—SO$_2$-alkyl, and —NH—SO$_2$-cycloalkyl;

when the aryl group is substituted, the aryl group is substituted with 1 to 3 substituents independently selected from the group consisting of halogen, nitro, cyano, hydroxy, alkyl, alkenyl, perhaloalkyl, cycloalkyl, cycloalkenyl, heterocycle, —O-alkyl, —O-perhaloalkyl, —N(alkyl)alkyl, —N(H)alkyl, —NH$_2$, —SO$_2$-alkyl, —SO$_2$-perhaloalkyl, —N(alkyl)C(=O)alkyl, —N(H)C(=O)alkyl, —C(=O)N(alkyl)alkyl, —C(=O)N(H)alkyl, —C(=O)NH$_2$, —SO$_2$N(alkyl)alkyl, —SO$_2$N(H)alkyl, —SO$_2$NH$_2$, —NH—SO$_2$-alkyl, and —NH—SO$_2$-cycloalkyl;

when the heteroaryl group is substituted, the heteroaryl group is substituted with 1 to 3 substituents independently selected from the group consisting of halogen, nitro, cyano, hydroxy, alkyl, alkenyl, perhaloalkyl, cycloalkyl, cycloalkenyl, heterocycle, —O-alkyl, —O-perhaloalkyl, —N(alkyl)alkyl, —N(H)alkyl, —NH$_2$, —SO$_2$-alkyl, —SO$_2$-perhaloalkyl, —N(alkyl)C(=O)alkyl, —N(H)C(=O)alkyl, —C(=O)N(alkyl)alkyl, —C(=O)N(H)alkyl, —C(=O)NH$_2$, —SO$_2$N(alkyl)alkyl, —SO$_2$N(H)alkyl, —SO$_2$NH$_2$, —NH—SO$_2$-alkyl, and —NH—SO$_2$-cycloalkyl;

when the heterocyclyl group is substituted, the heterocyclyl group is substituted with 1 to 3 substituents, when the heterocyclic group is substituted on a ring carbon of the 'heterocycle', the substituents are independently selected from the group consisting of halogen, nitro, cyano, oxo, alkyl, alkenyl, perhaloalkyl, cycloalkyl, cycloalkenyl, aryl, heteroaryl, heterocyclyl, —OR$^{10b}$, —C(=O)OR$^{10a}$, —OC(=O)R$^{10a}$, —C(=O)N(H)R$^{10}$, —C(=O)N(alkyl)R$^{10}$, —N(H)C(=O)R$^{10a}$, —N(H)R$^{10}$, —N(alkyl)R$^{10}$, —N(H)C(=O)N(H)R$^{10}$, and —N(H)C(=O)N(alkyl)R$^{10}$;

when the heterocyclic group is substituted-on a ring nitrogen of the 'heterocycle', substituents are independently selected from the group consisting of alkyl, alkenyl, cycloalkyl, cycloalkenyl, aryl, heteroaryl, —SO$_2$R$^{10a}$, —C(=O)R$^{10a}$, C(=O)OR$^{10a}$, —C(=O)N(H)R$^{10}$, —C(=O)N(alkyl)R$^{10}$, —NH—SO$_2$-alkyl and —NH—SO$_2$-cycloalkyl;

R$^{10}$ is selected from the group consisting of hydrogen, alkyl, alkenyl, cycloalkyl, cycloalkenyl, aryl, heteroaryl, and heterocyclyl;

R$^{10a}$ is selected from the group consisting of alkyl, alkenyl, perhaloalkyl, cycloalkyl, cycloalkenyl, aryl, heteroaryl, and heterocyclyl; and R$^{10b}$ is selected from the group consisting of hydrogen, alkyl, alkenyl, perhaloalkyl, cycloalkyl, cycloalkenyl, aryl, heteroaryl, and heterocyclyl;

wherein the compound of formula Ib includes a tautomeric form thereof, a stereoisomeric form thereof, or a pharmaceutically acceptable salt thereof.

4. A method for inhibiting an MEK kinase, said method comprising:

administering a composition to an individual in need of said inhibiting; wherein the composition comprises an effective amount of a compound of formula Ic and optionally one or more pharmaceutically acceptable carriers, diluents, or excipients; and wherein the compound of formula Ic is represented by the following structure

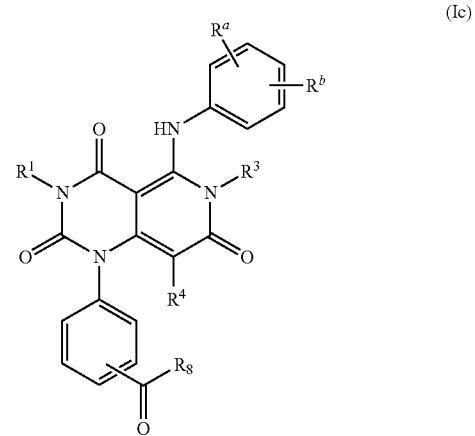

(Ic)

wherein,

R$^1$ is selected from the group consisting of hydrogen, substituted- or unsubstituted-alkyl, substituted- or unsubstituted-cycloalkyl, and substituted- or unsubstituted-heterocyclyl;

R$^3$ is selected from the group consisting of hydrogen, substituted- or unsubstituted-alkyl, and substituted- or unsubstituted-cycloalkyl;

R$^4$ is selected from the group consisting of hydrogen, halogen, substituted- or unsubstituted-alkyl, and substituted- or unsubstituted-cycloalkyl;

R$^a$ and R$^b$ are selected from the group consisting of hydrogen, halogen, and haloalkyl;

R$^8$ is selected from the group consisting of substituted- or unsubstituted-alkyl, substituted- or unsubstituted-alkenyl, substituted- or unsubstituted-alkynyl, substituted- or unsubstituted-cycloalkyl, and substituted- or unsubstituted-cycloalkenyl;

when the alkyl group and alkenyl group is substituted, the alkyl group and alkenyl group is substituted with 1 to 4 substituents independently selected from the group consisting of oxo, halogen, nitro, cyano, perhaloalkyl, cycloalkyl, aryl, heteroaryl, heterocyclyl, —OR$^{10b}$, —SO$_2$R$^{10a}$, —C(=O)OR$^{10a}$, —OC(=O)R$^{10a}$, —C(=O)N(H)R$^{10}$, —OR$^{10a}$, —C(=O)N(alkyl)R$^{10}$, —N(H)C(=O)R$^{10a}$, —N(H)R$^{10}$, —N(alkyl)R$^{10}$, —N(H)C(=O)N(H)R$^{10}$, —N(H)C(=O)N(alkyl)R$^{10}$, —NH—SO$_2$-alkyl, and —NH—SO$_2$-cycloalkyl;

when the cycloalkyl group and cycloalkenyl group is substituted, the cycloalkyl group and cycloalkenyl group is substituted with 1 to 3 substituents independently selected from the group consisting of oxo, halogen, nitro, cyano, alkyl, alkenyl, perhaloalkyl, aryl, heteroaryl, heterocyclyl, —OR$^{10b}$, —SO$_2$R$^{10a}$, —C(=O)R$^{10a}$, —C(=O)OR$^{10a}$, —OC(=O)R$^{10a}$, —C(=O)N(H)R$^{10}$, —C(=O)N(alkyl)R$^1$, —N(H)C(=O)R$^{10a}$, —N(H)R$^{10}$, —N(alkyl)R$^{10}$, —N(H)C(=O)N(H)R$^{10}$, —N(H)C(=O)N(alkyl)R$^{10}$, —NH—SO$_2$-alkyl, and —NH—SO$_2$-cycloalkyl;

when the aryl group is substituted, the aryl group is substituted with 1 to 3 substituents independently selected from the group consisting of halogen, nitro, cyano, hydroxy, alkyl, alkenyl, perhaloalkyl, cycloalkyl, cycloalkenyl, heterocycle, —O-alkyl, —O-perhaloalkyl, —N(alkyl)alkyl, —N(H)alkyl, —NH$_2$, —SO$_2$-alkyl, —SO$_2$-perhaloalkyl, —N(alkyl)C(=O)alkyl, —N(H)C(=O)alkyl, —C(=O)N(alkyl)alkyl, —C(=O)N(H)alkyl, —C(=O)NH$_2$, —SO$_2$N(alkyl)alkyl, —SO$_2$N(H)alkyl, —SO$_2$NH$_2$, —NH—SO$_2$-alkyl, and —NH—SO$_2$-cycloalkyl;

when the heteroaryl group is substituted, the heteroaryl group is substituted with 1 to 3 substituents independently selected from the group consisting of halogen, nitro, cyano, hydroxy, alkyl, alkenyl, perhaloalkyl, cycloalkyl, cycloalkenyl, heterocycle, —O-alkyl, O-perhaloalkyl, —N(alkyl)alkyl, —N(H)alkyl, —NH$_2$, —SO$_2$-alkyl, —SO$_2$-perhaloalkyl, —N(alkyl)C(=O)alkyl, —N(H)C(=O)alkyl, —C(=O)N(alkyl)alkyl, —C(=O)N(H)alkyl, —C(=O)NH$_2$, —SO$_2$N(alkyl)alkyl, —SO$_2$N(H)alkyl, —SO$_2$NH$_2$, —NH—SO$_2$-alkyl, and —NH—SO$_2$-cycloalkyl;

when the heterocyclyl group is substituted, the heterocyclyl group is substituted with 1 to 3 substituents, when the heterocyclic group is substituted on a ring carbon of the 'heterocycle', the substituents are independently selected from the group consisting of halogen, nitro, cyano, oxo, alkyl, alkenyl, perhaloalkyl, cycloalkyl, cycloalkenyl, aryl, heteroaryl, heterocyclyl, —OR$^{10b}$, C(=O)OR$^{10a}$, —OC(=O)R$^{10a}$, —C(=O)N(H)R$^{10}$, —C(=O)N(alkyl)R$^{10}$, —N(H)C(=O)R$^{10a}$, —N(H)R$^{10}$, —N(alkyl)R$^{10}$, —N(H)C(=O)N(H)R$^{10}$, and —N(H)C(=O)N(alkyl)R$^{10}$;

when the heterocyclic group is substituted on a ring nitrogen of the 'heterocycle', substituents are independently selected from the group consisting of alkyl, alkenyl, cycloalkyl, cycloalkenyl, aryl, heteroaryl, —SO$_2$R$^{10a}$, —C(=O)R$^{10a}$, C(=O)OR$^{10a}$, —C(=O)N(H)R$^{10}$, —C(=O)N(alkyl)R$^{10}$, —NH—SO$_2$-alkyl and —NH—SO$_2$-cycloalkyl;

R$^{10}$ is selected from the group consisting of hydrogen, alkyl, alkenyl, cycloalkyl, cycloalkenyl, aryl, heteroaryl, and heterocyclyl;

R$^{10a}$ is selected from the group consisting of alkyl, alkenyl, perhaloalkyl, cycloalkyl, cycloalkenyl, aryl, heteroaryl, and heterocyclyl; and R$^{10b}$ is selected from the group consisting of hydrogen, alkyl, alkenyl, perhaloalkyl, cycloalkyl, cycloalkenyl, aryl, heteroaryl, and heterocyclyl;

wherein the compound of formula Ic includes a tautomeric form thereof, a stereoisomeric form thereof, or a pharmaceutically acceptable salt thereof.

5. The method compound of claim 1, wherein R$^1$ is selected from the group consisting of hydrogen, alkyl, and cycloalkyl.

6. The method of claim 1, wherein R$^1$ is selected from the group consisting of hydrogen, methyl, and cyclopropyl.

7. The method of claim 1, wherein R$^3$ is methyl.

8. The method of claim 1, wherein R$^4$ is selected as methyl.

9. The method of claim 1, wherein R$^a$ and R$^b$ are halogen.

10. The method of claim 1, wherein R$^a$ and R$^b$ are independently fluorine and iodine.

11. The method of claim 1, wherein R$^6$ is selected from the group consisting of direct bond, —[C(R$^c$)R$^d$]$_n$NR$^9$—, —[C(R$^c$)R$^d$]$_n$O—, and —NHC(=O)[C(R$^c$)R$^d$]$_p$.

12. The method of claim 1, wherein R$^6$ is selected from the group selected from direct bond, —NH—, —O—, —CH$_2$O—, and —NHC(=O)—.

13. The method of claim 1, wherein E is selected from the group consisting of 3-oxetane, 1-azetidine, 1-azetidine-2-one, and 3-azetidine substituted- or unsubstituted-with methyl, fluoro, —C(=O)OR$^e$, and —OR$^e$; wherein R$^e$ is hydrogen, tert-butyl, and —CH$_2$C(=O)NH$_2$.

14. The method of claim 1, wherein R$^7$ is cyclopropyl.

15. The method of claim 1, wherein R$^8$ is cyclopropyl.

16. The method of claim 1, wherein R$^1$ is selected from the group consisting of hydrogen, alkyl, and cycloalkyl; R$^3$ is alkyl; R$^4$ is alkyl; R$^a$ and R$^b$ are halogen; R$^6$ is selected from the group consisting of direct bond, —[C(R$^c$)R$^d$]$_n$NR$^9$—, —[C(R$^c$)R$^d$]$_n$O—, and —NHC(=O)[C(R$^c$)R$^d$]$_p$;

E is substituted- or unsubstituted-four membered heterocyclic ring; R$^7$ is substituted- or unsubstituted-cycloalkyl; R$^8$ is substituted- or unsubstituted-cycloalkyl.

17. The method of claim 1, wherein R$^1$ is selected from the group consisting of hydrogen, methyl, and cyclopropyl; R$^3$ is methyl; R$^4$ is methyl; R$^a$ and R$^b$ are independently fluoro and iodo; R$^6$ is direct bond, —NH—, —O—, —CH$_2$O—, and —NHC(=O)—; E is 3-oxetane, 1-azetidine, 1-azetidine-2-one, and 3-azetidine substituted- or unsubstituted-with methyl, fluoro, tert-butoxy carbonyl, —OH, and —OCH$_2$C(=O)NH$_2$; R$^7$ is cyclopropyl and R$^8$ is cyclopropyl.

18. A method for inhibiting an MEK kinase, said method comprising:

administering a composition to an individual in need of said inhibiting, wherein the composition comprises an effective amount of a compound, its tautomeric forms, or its pharmaceutically acceptable salts thereof, wherein the compound is selected from the group consisting of:

1-(3-(cyclopropylsulfonyl)phenyl)-5-((2-fluoro-4-iodophenyl)amino)-6,8-dimethyl pyrido [4,3-d]pyrimidine-2,4,7(1H,3H,6H)-trione (Compound 1)

3-cyclopropyl-5-((2-fluoro-4-iodophenyl)amino)-1-(3-(3-hydroxyazetidin-1-yl)phenyl)-6,8-dimethylpyrido [4,3-d]pyrimidine-2,4,7(1H,3H,6H)-trione (Compound 2)

3-cyclopropyl-1-(3-(cyclopropylsulfonyl)phenyl)-5-((2-fluoro-4-iodophenyl)amino)-6,8-dimethylpyrido[4,3-d]pyrimidine-2,4,7(1H,3H,6H)-trione (Compound 3)

3-cyclopropyl-5-((2-fluoro-4-iodophenyl)amino)-6,8-dimethyl-1-(3-(2-oxoazetidin-1-yl)phenyl)pyrido[4,3-d]pyrimidine-2,4,7(1H,3H,6H)-trione (Compound 4)

3-cyclopropyl-5-((2-fluoro-4-iodophenyl)amino)-6,8-dimethyl-1-(3-(oxetan-3-ylamino) phenyl)pyrido[4,3-d]pyrimidine-2,4,7(1H,3H,6H)-trione (Compound 5)

3-cyclopropyl-5-((2-fluoro-4-iodophenyl)amino)-6,8-dimethyl-1-(3-(oxetan-3-yloxy) phenyl)pyrido[4,3-d]pyrimidine-2,4,7(1H,3H,6H)-trione (Compound 7)

1-(3-(azetidin-1-yl)phenyl)-3-cyclopropyl-5-((2-fluoro-4-iodophenyl)amino)-6,8-dimethyl pyrido[4,3-d]pyrimidine-2,4,7(1H,3H,6H)-trione (Compound 8)

3-cyclopropyl-5-((2-fluoro-4-iodophenyl)amino)-1-(3-(3-hydroxyoxetan-3-yl)phenyl)-6,8-dimethylpyrido[4,3-d]pyrimidine-2,4,7(1H,3H,6H)-trione (Compound 9)

N-(3-(3-cyclopropyl-5-((2-fluoro-4-iodophenyl)amino)-6,8-dimethyl-2,4,7-trioxo-3,4,6,7-tetrahydropyrido[4,3-d]pyrimidin-1(2H)-yl)phenyl)-3-methyloxetane-3-carboxamide (Compound 10)

1-(3-(cyclopropanecarbonyl)phenyl)-3-cyclopropyl-5-((2-fluoro-4-iodophenyl)amino)-6,8-dimethylpyrido[4,3-d]pyrimidine-2,4,7(1H,3H,6H)-trione (Compound 11)

1-(3-(cyclopropylsulfonyl)phenyl)-5-((2-fluoro-4-iodophenyl)amino)-3,6,8-trimethyl pyrido[4,3-d]pyrimidine-2,4,7(1H,3H,6H)-trione (Compound 12)

5-((2-fluoro-4-iodophenyl)amino)-3,6,8-trimethyl-1-(3-((oxetan-3-yloxy)methyl) phenyl)pyrido[4,3-d]pyrimidine-2,4,7(1H,3H,6H)-trione (Compound 13)

5-((2-fluoro-4-iodophenyl)amino)-1-(3-(3-hydroxyoxetan-3-yl)phenyl)-3,6,8-trimethylpyrido[4,3-d]pyrimidine-2,4,7(1H,3H,6H)-trione (Compound 14)

5-((2-fluoro-4-iodophenyl)amino)-3,6,8-trimethyl-1-(3-(oxetan-3-yloxy)phenyl) pyrido[4,3-d]pyrimidine-2,4,7(1H,3H,6H)-trione (Compound 15)

1-(3-(azetidin-1-yl)phenyl)-5-((2-fluoro-4-iodophenyl)amino)-3,6,8-trimethylpyrido[4,3-d]pyrimidine-2,4,7(1H,3H,6H)-trione (Compound 16)

5-((2-fluoro-4-iodophenyl)amino)-3,6,8-trimethyl-1-(3-(oxetan-3-ylamino)phenyl) pyrido[4,3-d]pyrimidine-2,4,7(1H,3H,6H)-trione (Compound 17)

N-(3-(5-((2-fluoro-4-iodophenyl)amino)-3,6,8-trimethyl-2,4,7-trioxo-3,4,6,7-tetrahydro pyrido[4,3-d]pyrimidin-1 (2H)-yl)phenyl)-3-methyloxetane-3-carboxamide (Compound 18)

2-((1-(3-(5-((2-fluoro-4-iodophenyl)amino)-3,6,8-trimethyl-2,4,7-trioxo-3,4,6,7-tetra hydropyrido[4,3-d]pyrimidin-1(2H)-yl)phenyl)azetidin-3-yl)oxy)acetamide (Compound 19)

5-((2-fluoro-4-iodophenyl)amino)-1-(3-(3-fluorooxetan-3-yl)phenyl)-3,6,8-trimethyl pyrido[4,3-d]pyrimidine-2,4,7(1H,3H,6H)-trione (Compound 20)

N-(3-(3-cyclopropyl-5-((2-fluoro-4-iodophenyl)amino)-6,8-dimethyl-2,4,7-trioxo-3,4,6,7-tetrahydropyrido[4,3-d]pyrimidin-1(2H)-yl)phenyl)azetidine-3-carboxamide (Compound 21).

19. The method of claim 1, wherein the individual suffers from an MEK mediated disorder selected from the group consisting of an inflammatory disease, an infection, an autoimmune disorder, an ischemia, a cardiac disorder, a neurological disorder, a fibrogenetic disorder, a proliferative disorder, a metabolic disease, and a malignant disease.

20. The method of claim 19, wherein said MEK mediated disorder is a hyperproliferative disease.

21. The method of claim 19, wherein said hyperproliferative disease is a cancer or a tumor.

22. The method of claim 19, wherein said MEK mediated disorder is an inflammatory disease.

23. The method of claim 19, wherein said individual is a mammal.

24. The method of claim 19, wherein the MEK mediated disorder is a proliferative disease.

25. The method of claim 24, wherein said proliferative disease is a cancer and said cancer is a tumor, a leukemia, or a carcinoma.

26. The method of claim 22, wherein said inflammatory disease is rheumatoid arthritis or multiple sclerosis.

27. The method of claim 18, wherein the individual suffers from an MEK mediated disorder selected from the group consisting of an inflammatory disease, an infection, an autoimmune disorder, an ischemia, a cardiac disorder, a neurological disorder, a fibrogenetic disorder, a proliferative disorder, a metabolic disease, and a malignant disease.

28. The method of claim 27, wherein said MEK mediated disorder is a hyperproliferative disease.

29. The method of claim 28, wherein said hyperproliferative disease is a cancer and said cancer is a tumor, a leukemia, or a carcinoma.

30. The method of claim 29, wherein said individual is a mammal.

31. The method of claim 27, wherein said MEK mediated disorder is a stroke.

32. The method of claim 19, wherein said MEK mediated disorder is a stroke.

\* \* \* \* \*

UNITED STATES PATENT AND TRADEMARK OFFICE
CERTIFICATE OF CORRECTION

PATENT NO. : 9,827,247 B2  
APPLICATION NO. : 15/400627  
DATED : November 28, 2017  
INVENTOR(S) : Bhavesh Dave et al.

Page 1 of 1

It is certified that error appears in the above-identified patent and that said Letters Patent is hereby corrected as shown below:

In the Claims

In Claim 21, Column 54, Line 7, please correct the claim dependency:  
21. The method of claim 19, wherein said hyperprolif-  
Should read:  
21. The method of claim 20, wherein said hyperprolif- Signed and Sealed this  
Twenty-fifth Day of September, 2018

Andrei Iancu  
*Director of the United States Patent and Trademark Office*